(12) United States Patent
Camacho et al.

(10) Patent No.: US 8,805,701 B2
(45) Date of Patent: Aug. 12, 2014

(54) SYSTEM, METHOD AND COMPUTER PROGRAM PRODUCT FOR ENABLING A CUSTOMER TO SELECT A CARE PATH FOR TREATMENT OF A MEDICAL INDICATION, TO SELECT PROVIDERS BASED ON QUALITY AND COST AND TO ESTIMATE MEDICAL COSTS

(75) Inventors: Godofredo T. Camacho, St. Paul, MN (US); Karl J. Ulfers, Minneapolis, MN (US); Imad Ahmed, North Oaks, MN (US); Lauri R. Middleton, Cape Neddick, ME (US)

(73) Assignee: UnitedHealth Group Incorporated, Minnetonka, MN (US)

( * ) Notice: Subject to any disclaimer, the term of this patent is extended or adjusted under 35 U.S.C. 154(b) by 128 days.

(21) Appl. No.: 13/354,019

(22) Filed: Jan. 19, 2012

(65) Prior Publication Data

US 2013/0191135 A1   Jul. 25, 2013

(51) Int. Cl.
*G06Q 50/22* (2012.01)
(52) U.S. Cl.
USPC .................................. 705/2; 705/3
(58) Field of Classification Search
USPC ........................................ 705/2–3
See application file for complete search history.

(56) References Cited

U.S. PATENT DOCUMENTS

| | | |
|---|---|---|
| 5,225,976 A | 7/1993 | Tawil |
| 5,845,254 A | 12/1998 | Lockwood et al. |
| 5,915,241 A | 6/1999 | Giannini |
| 6,061,657 A | 5/2000 | Whiting-O'Keefe |
| 6,735,569 B1 | 5/2004 | Wizig |
| 6,895,445 B2 | 5/2005 | Ying et al. |
| 7,343,565 B2 | 3/2008 | Ying et al. |
| 7,383,197 B1 * | 6/2008 | Neuman ........................... 705/3 |
| 7,505,916 B1 | 3/2009 | Adrian et al. |
| 7,747,644 B1 | 6/2010 | Reihl et al. |
| 8,005,687 B1 | 8/2011 | Pederson et al. |
| 2002/0147617 A1 | 10/2002 | Schoenbaum et al. |

(Continued)

FOREIGN PATENT DOCUMENTS

| | | |
|---|---|---|
| JP | 2003-288411 A | 10/2003 |
| KR | 10-2009-0072550 A | 7/2009 |
| KR | 10-2011-0112901 A | 10/2011 |

OTHER PUBLICATIONS

AHRQ (Agency for Healthcare Research and Quality), Ambulatory Surgery in U.S. Hospitals, 2003, www.ahrq.gov, www.ahrq.gov/data/hcup/factbk9/factbk9e.htm.

(Continued)

*Primary Examiner* — John Pauls
*Assistant Examiner* — Jason Tiedeman
(74) *Attorney, Agent, or Firm* — Dorsey & Whitney LLP

(57) ABSTRACT

In one embodiment, disclosed herein is a method for selecting a treatment care path. The method includes receiving identification of a health condition and at least one medical outcome after treatment of the health condition. Further, the method includes identifying at least one medical treatment to achieve the medical outcome, the treatment care path including the at least one or medical treatment. Additionally, the method includes identifying one or more treatment options for each of the at least one medical treatment; and providing a cost estimate for each of the one or more treatment options. Finally, the method includes optimizing the treatment care path by, for each of the at least one medical treatments, selecting one or more treatment options based on the cost estimate thereof.

26 Claims, 17 Drawing Sheets

(56) References Cited

U.S. PATENT DOCUMENTS

| | | |
|---|---|---|
| 2003/0097279 A1 | 5/2003 | deLusignan et al. |
| 2007/0088580 A1 | 4/2007 | Richards Jr. |
| 2008/0172251 A1 | 7/2008 | Reichert et al. |
| 2008/0263477 A1 | 10/2008 | Ying et al. |
| 2011/0055185 A1 | 3/2011 | Bitan et al. |
| 2011/0238441 A1 | 9/2011 | Callas |
| 2011/0270625 A1 | 11/2011 | Pederson et al. |
| 2011/0301977 A1 | 12/2011 | Belcher et al. |
| 2012/0101847 A1 | 4/2012 | Johnson et al. |

OTHER PUBLICATIONS

"Preference-Sensitive Care," A Dartmouth Atlas Project Topic Brief, www.dartmouthatlas.org, Lebanon, NH, p. 1-6. Jan. 15, 2007.

Guide to History Taking and Examination, Oct. 2009, University College London Medical School, p. 2-9.

\* cited by examiner

Fig. 11B

| | HOW IT WORKS | CARE ESTIMATES | ▽ LOG OFF PRESCRIPTION ESTIMATES |
|---|---|---|---|
| CARE ESTIMATE: LAMINECTOMY | OUT OF POCKET MEANS AVERAGE | $ 3 3 7 5 | TOTAL COST GENERAL AVERAGE $ 1 1 6 7 5 |

⌂  ⊗☺ $50  ⊗🏢$100  ⊗☺ $100  ⊗☺ $50  ⊗🏢$3000  ⊗☺ $50  [$]
ASSESS  DR. VISIT  RADIOLOGY & LAB WORK  MANIPULATION & EXERCISE       PHYSICAL THERAPY
LAMINECTOMY  DR. GREENWALD  ABC RADIOLOGY  DR. SMITH  [REFINE DOCTOR]  STEP 5  STEP 6  FINISH

ORTHOPEDIC SURGEON MONTH 3           🖨 PRINT  ✉ EMAIL  ✓ SAVE

+ WHAT DO I NEED TO KNOW ABOUT C CHOOSING AN ORTHOPEDIC SURGEON?

SEARCH BY: [CITY, STATE OR ZIP CODE] [WITHIN 5 MILES ▽] [GO] [SPECIALTIES ▽]  CHOOSE UP TO 5 DOCTORS TO COMPARE
[PHYSICIAN NAME]  ☑M ☑F  [LANGUAGES ▽]  [+][+][ ][ ]  [COMPARE]

YOUR SEARCH RETURNED (5) DOCTORS RANGING FROM LOWEST $0000 TO HIGHEST $0000
SORT BY: [PREMIUM DESIGNATION ▽]  VIEW: [5 PER PAGE ▽]        CURRENTLY VIEWING 1-5 OF 5

DR. ERICKSON  ORTHOPEDIC SURGEON ★★ [?] WHAT IS THIS? • IN NETWORK 1.00 MILES FROM 55401  ADD TO COMPARE ☐
1234 MAIN STREET      LOCAL      THIS PHYSICIAN  EMPLOYER   OUT-OF-POCKET↵  ASSOCIATED
MINNEAPOLIS MN 55401  AVERAGE    $250            PAYS       $50              FACILITIES        [ADD AS MY DOCTOR ▷]
612-999-9999          $250       MATCH AVERAGE   $200                        $10,000-$12,000
+ DISPLAY ADDITIONAL INFORMATION

DR. CHANDLER  GENERAL SURGEON  ★★ [?] WHAT IS THIS? • IN NETWORK 1.00 MILES FROM 55401  ADD TO COMPARE ☐
1234 MAIN STREET      LOCAL      THIS PHYSICIAN  EMPLOYER   OUT-OF-POCKET ↵  ASSOCIATED
MINNEAPOLIS MN 55401  AVERAGE    $225            PAYS       $25              FACILITIES        [ADD AS MY DOCTOR ▷]
612-999-9999          $250       BELOW AVERAGE   $200                        $8,500-$14,425
+ DISPLAY ADDITIONAL INFORMATION

DR. SMITH  GENERAL SURGEON  ★☆ [?] WHAT IS THIS? • IN NETWORK 1.00 MILES FROM 55401  ADD TO COMPARE ☐
1234 MAIN STREET      LOCAL      THIS PHYSICIAN  EMPLOYER   OUT-OF-POCKET ↵  ASSOCIATED
MINNEAPOLIS MN 55401  AVERAGE    $250            PAYS       $75              FACILITIES        [ADD AS MY DOCTOR ▷]
612-999-9999          $250       MATCH AVERAGE   $175                        $10,000-$12,300
+ DISPLAY ADDITIONAL INFORMATION

DR. SCHWARTZ  GENERAL SURGEON  ★☆ [?] WHAT IS THIS? • IN NETWORK 1.00 MILES FROM 55401  ADD TO COMPARE ☐
1234 MAIN STREET      LOCAL      THIS PHYSICIAN  EMPLOYER   OUT-OF-POCKET ↵  ASSOCIATED
MINNEAPOLIS MN 55401  AVERAGE    $275            PAYS       $50              FACILITIES        [ADD AS MY DOCTOR ▷]
612-999-9999          $250       ABOVE AVERAGE   $225                        $12,300-$14,300
+ DISPLAY ADDITIONAL INFORMATION

DR. WISEN  GENERAL SURGEON  ☆☆ [?] WHAT IS THIS? • IN NETWORK 1.00 MILES FROM 55401  ADD TO COMPARE ☐
1234 MAIN STREET      LOCAL      THIS PHYSICIAN  EMPLOYER   OUT-OF-POCKET ↵  ASSOCIATED
MINNEAPOLIS MN 55401  AVERAGE    $325            PAYS       $50              FACILITIES        [ADD AS MY DOCTOR ▷]
612-999-9999          $250       ABOVE AVERAGE   $275                        $12,300-$13,250
+ DISPLAY ADDITIONAL INFORMATION

BACK TO TOP ▲                                          CURRENTLY VIEWING 1-5 OF 5

Fig. 11C

SYSTEM, METHOD AND COMPUTER PROGRAM PRODUCT FOR ENABLING A CUSTOMER TO SELECT A CARE PATH FOR TREATMENT OF A MEDICAL INDICATION, TO SELECT PROVIDERS BASED ON QUALITY AND COST AND TO ESTIMATE MEDICAL COSTS

CROSS REFERENCE TO RELATED APPLICATION

This application incorporates by reference in their entirety the disclosures of U.S. application Ser. No. 10/966,530, filed Oct. 15, 2004, now U.S. Pat. No. 8,005,687, which claims the benefit under 35 U.S.C. §119(e) to U.S. Provisional Application No. 60/512,006 entitled "SYSTEM, METHOD AND COMPUTER PROGRAM PRODUCT FOR ESTIMATING MEDICAL COSTS," filed Oct. 15, 2003.

FIELD OF THE INVENTION

The present disclosure relates to a system, method, and computer program product that provides care path information for a medical condition or medical indication from which a consumer may select a care path, provides information on providers to enable consumers to select providers, and provides cost information related to care paths.

BACKGROUND OF THE INVENTION

As will be appreciated by those having ordinary skill in the art, there may be numerous treatment possibilities for any given medical condition. For example, there are numerous medications available for the treatment of certain cardiac conditions, such as high blood pressure, high cholesterol, or other cardiac conditions. Alternatively, non-medication avenues for treatment may be available, such as surgery. What is needed therefore are systems and methods to help the healthcare consumer choose and evaluate the quality and/or cost of various healthcare options to achieve targeted medical goals.

Also, each treatment option may have one or more providers available to provide treatment. Currently, it is very difficult for a consumer to select one or more providers. There is a need for a system to enable consumers to select providers. Consumers need to have access to information that helps them select among available providers based on quality and/or cost, for example.

Furthermore, there are costs associated with each treatment option. Depending on the consumer's budget, certain treatment options may be more affordable. There is a need for a system that provides cost information for each step involved in a treatment option.

What is further needed is a system and method for providing consumers with health treatment options, based on quality and cost estimates, to provide the consumer greater clarity in selecting from among a variety of medical treatment options.

In short, healthcare consumers have an increasing need to find value in their search for quality healthcare options. Healthcare consumers have an increasing need for transparency in their search for healthcare options. Moreover, with regard to a given health care option, healthcare consumers have a need to understand the costs involved in each of the steps involved in a particular healthcare option.

SUMMARY OF THE INVENTION

In one embodiment, disclosed herein is a method for selecting a treatment care path. The method includes receiving identification of a health condition and at least one medical outcome after treatment of the health condition. Further, the method includes identifying at least one medical treatment to achieve the medical outcome, the treatment care path including the at least one or medical treatment. Additionally, the method includes identifying one or more treatment options for each of the at least one medical treatment; and providing a cost estimate for each of the one or more treatment options. Finally, the method includes optimizing the treatment care path by, for each of the at least one medical treatments, selecting one or more treatment options based on the cost estimate thereof.

In another embodiment disclosed herein, a system to generate at least one medical treatment care path in response to receiving a health condition and at least one medical outcome after treatment of the health condition is disclosed. The system comprises computer-executable instructions to identify at least one medical treatment to achieve the medical outcome. The treatment care path includes at least one medical treatment; computer-executable instructions to identify one or more treatment options for each of the at least one medical treatment; computer-executable instructions to provide a cost estimate for each of the one or more treatment options; and computer-executable instructions to display at least one care path as an optimal treatment care path by selecting at least one of the medical treatments based on at least one of cost and quality.

BRIEF DESCRIPTION OF THE DRAWINGS

FIG. 11B illustrates information provided on a user display related to a particular care path in accordance with one embodiment of the present disclosure.

FIG. 11C illustrates information provided on a user display related to choosing a particular provider in accordance with one embodiment of the present disclosure.

DETAILED DESCRIPTION

Figure 1:
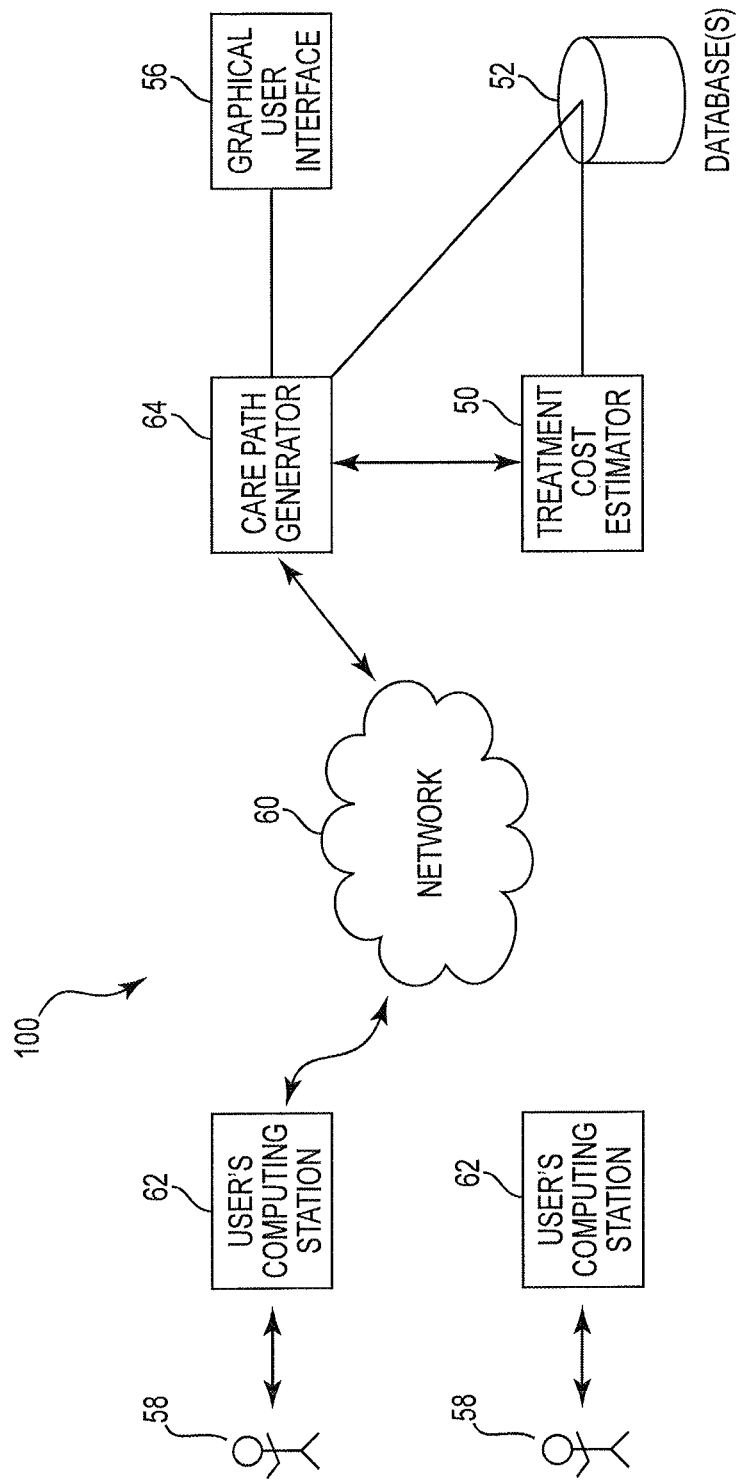
FIG. 1 illustrates an example of a block diagram of a care path generator application accessible to users over a network, in accordance with one embodiment of the present disclosure.

The present disclosure discloses a system, method, and computer product that, in one embodiment, will provide consumers with information about various treatment options as well as information about each of the steps included in the care path involved in a particular treatment option. In this aspect of the present disclosure, a healthcare consumer may use this information to make an informed decision about which healthcare option to select, including which care path. As such, this information enables the healthcare consumer to select a healthcare option that is best suited to his/her needs.

The present disclosure also discloses a system, method, and computer product that, in one embodiment, will provide consumers with information regarding providers for each step in a medical treatment option. The provider information may be based on quality and/or cost, for example. This information will enable a healthcare consumer to make an informed selection of one or more providers for a particular treatment option. Unless otherwise stated, the term "provider" as used herein may refer to one or more physicians and/or one or more facilities.

Furthermore, the present disclosure discloses a system, method, and computer product that, in one embodiment, will provide cost estimates for each step of a medical treatment option as well as an aggregate cost for the selected option as a whole. This cost estimate will preferably be based on average costs calculated from claim information from the providers involved as well as the facilities involved. The cost estimate may also be based on geographic averages. It will be understood, however, that the cost estimate may be based on any other relevant data sources or combination of sources.

In one aspect of the present disclosure, a system and method is provided that sets forth the available treatment options for a particular medical condition. Medical cost estimates are provided to the healthcare consumer, along with an expected health outcome of such treatment. In this manner, the healthcare consumer is able to more transparently see and compare the costs versus potential outcomes of various medical procedures to treat a condition.

Medical cost data may be provided by geographic region. Alternatively, and preferably, medical cost data may be provided by a database of prior claims. Further alternatively, and more preferably, medical cost data may be provided by a fee schedule of the provider. One or more sources of medical cost data may be used to provide a cost estimate in accordance with the present disclosure.

In a further aspect of medical cost data, it may be desirable, in some examples, to use "cross-platform" data, wherein the prior claims data of one entity is made available to another entity. As such, the claims data "pool" of information may be broader, and more accurate medical cost estimates may be desirably achieved.

It will further be appreciated that medical conditions may require more than one treatment. For example, a medical condition such as a broken leg may first require surgery, and may thereafter require outpatient therapy, medication, outpatient visits, or a combination of the above. As such, when evaluating a medical treatment option, the entire course of treatment may be evaluated, which may be referred to herein as a healthcare path. Thus, when the healthcare consumer evaluates the outcomes and costs of various methods of treatment, the entire path of a particular healthcare course of treatment may be evaluated to determine the overall costs, outcomes, and goals.

As discussed above, the treatments of a medical condition may generally be referred to as a course of treatment. A course of treatment may include a number of medical services, and a number of service categories, which may be offered by one or more medical professionals, and one or more medical facilities. The present disclosure has provided systems and methods for evaluating the costs of a particular treatment. Such treatment, as will be presently described, may be a part of a larger course of treatment, for any given category of medical service, provided by any medical professional, at any medical facility. For any course of treatment, one or more individual treatments may be combined, as discussed above, to achieve a desired result in a course of medical treatment. Such course of treatment may be given over time, and each component thereof may include an individual cost.

Referring to FIG. 1, a care path generator 64 for providing one or more care paths or portions thereof is illustrated in accordance with an embodiment of the present disclosure. As shown in FIG. 1, the care path generator 64 may be provided as a computer program (i.e., an application program) or hardware device accessing one or more databases 52 and/or other computer programs such as a treatment cost estimator 50 for calculating or estimating healthcare or medical treatment costs. It will be understood that the care path generator 64 may integrate a cost estimator as an integral part of the care path generator program, or the care path generator program may access and utilize one or more additional computer programs to determine cost estimates for one or more treatments. An exemplary treatment cost estimation program that may be integrated with or used in addition to the systems, methods, and computer products of the present disclosure is described in detail in U.S. application Ser. No. 10/966,530, filed Oct. 15, 2004, now U.S. Pat. No. 8,005,687, entitled "SYSTEM, METHOD AND COMPUTER PROGRAM PRODUCT FOR ESTIMATING MEDICAL COSTS," filed Oct. 15, 2003, which is hereby incorporated herein in its entirety. It will further be understood that the care path generator 64 may generate not only one or more care paths or portions thereof but may also generate other results related to one or more care paths as disclosed herein, for example the cost of one or more care paths and/or portions thereof, the optimal care path, etc. A graphical user interface 56, having one or more display screens, may also be provided or be in communication with the care path generator application 64, wherein the graphical user interface 56 provides users 58 with the ability to input data necessary for the care path generator 64 to generate one or more care paths or portions thereof, as well as to provides users 58 with various displays of the resulting data.

The one or more database 52 may access or include any suitable data that may be used to generate one or more care paths or portions thereof. Specifically, embodiments of the present disclosure may include databases with data related to one or more health plan members that may include information related to the member's medical coverage, medical conditions, medical history, etc.; databases with data related to one or more health plans including for example coverage amounts, deductibles, coinsurance, and/or copays, etc.; databases with data related to treatment including treatment options for particular conditions, illnesses and/or health states, etc.; databases with data related to cost data, for example, cost of services, which may be provided in a variety of different formats, for example cost of services by treatment, cost of services by provider, and/or cost of services by location or geography, for example; databases with data related to provider selection, for example provider cost, provider quality, provider outcomes data, and/or consumer feedback, for example. It will be understood that any other suitable data may be included in the systems, methods and products of the present disclosure.

Figure 2:
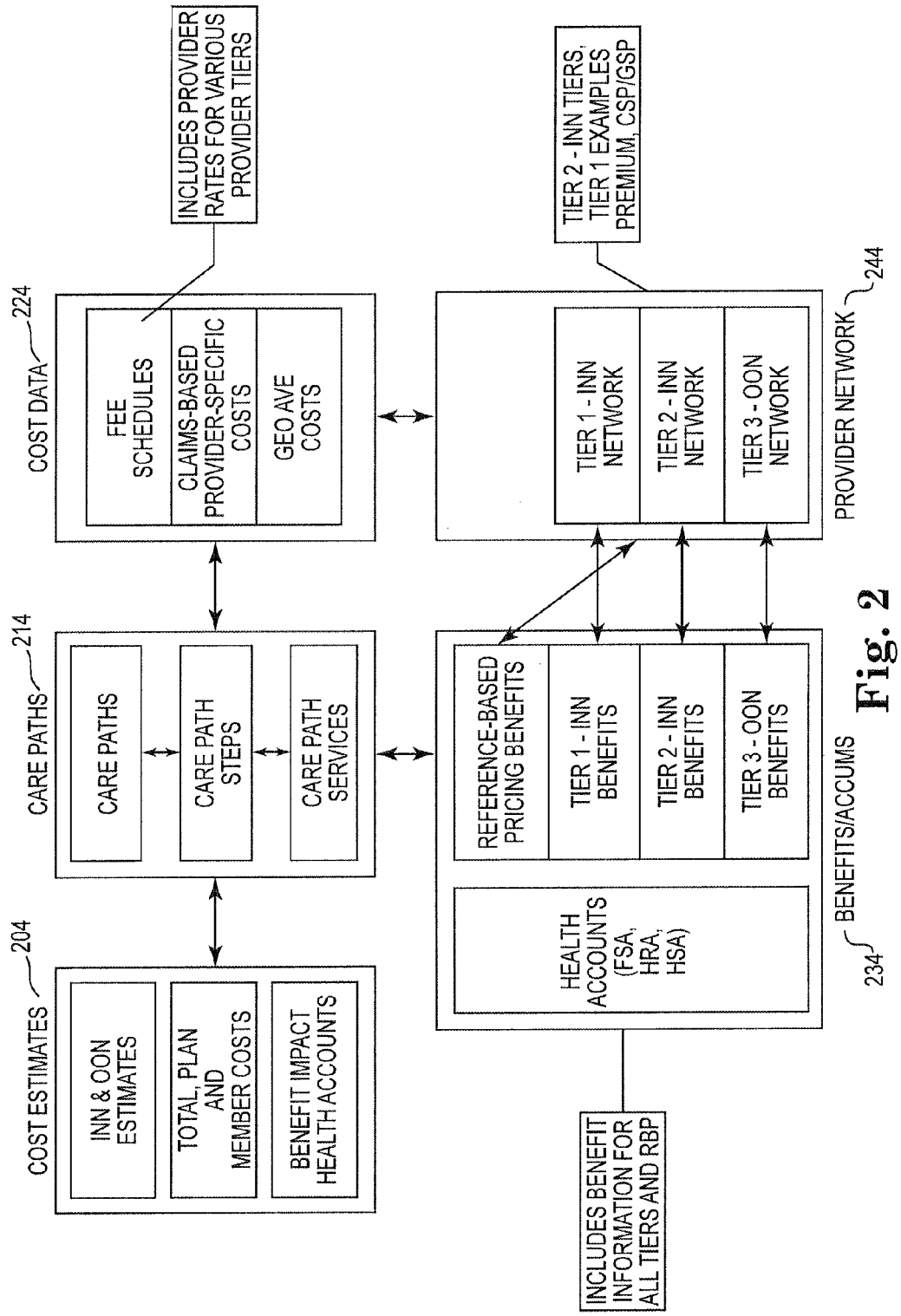
FIG. 2 illustrates various data sources and types that may be used in systems, methods, and products of the present disclosure, according to one embodiment.

FIG. 2 shows an embodiment of the types of linkages that may be included in the system between the various sources of data in order for the care path generator to provide desired outputs. As may be seen, generally five sources or types of data may be included in some embodiments of the system, data related to: cost estimates 204, which may include in-network and out-of-network estimates, total, plan and member costs, and benefit impact health accounts, for example; care paths 214, which may include data related to care paths, care path steps, and care path services, for example; cost data 224, which may include fee schedules, claims-based provider-specific costs (which may include episode of care data generated for example by means of a "grouper"), and geographical average costs; provider network data 244, which may include tier 1 in-network networks, tier 2 in-network networks, and tier 3 out-of-network networks data, for example; and benefits/accumulations data 234, which may include reference-based pricing benefits, tier 1 in-network benefits, tier 2 in-network benefits, and tier 3 out-of-network benefits, for example. While five sources and/or types of data have been described, it will be understood that any other suitable source or type of data may be incorporated into embodiments of the present disclosure. As may be seen, the various data sources and types may be advantageously linked to provide a system that provides care path outputs that may help a consumer make an informed, cost-effective, and/or appropriate decision related to their health care needs and/or goals.

With reference back to FIG. 1, the care path generator 64 is preferably accessible over a network 60, such as the Internet or any other conventional network including but not limited to Ethernets, wired or wireless networks or links, virtual private networks, or the like, for users 58 to access the care path generator 64 application program 64 and to view the results produced thereby. In one example, a user's computing station 62 is equipped with a browser program, such as Microsoft's Internet Explorer™, Netscape's Navigator™, a Linux browser, or other browsing application program, viewing program or other software, which provides the user 58 with access to the care path generator application program 64. The user's computing station 62 may be any conventional computing device or process, such as but not limited to a computer, personal data assistant (PDA), mobile phone, wireless device, tablet computer, terminal, or the like.

In another embodiment, the network 60 may be part of a company's intranet network wherein employees 58 access a care path generator program 64 through the company's intranet 60 in order to obtain one or more care paths or portions thereof and associated estimates for same.

Figure 3:
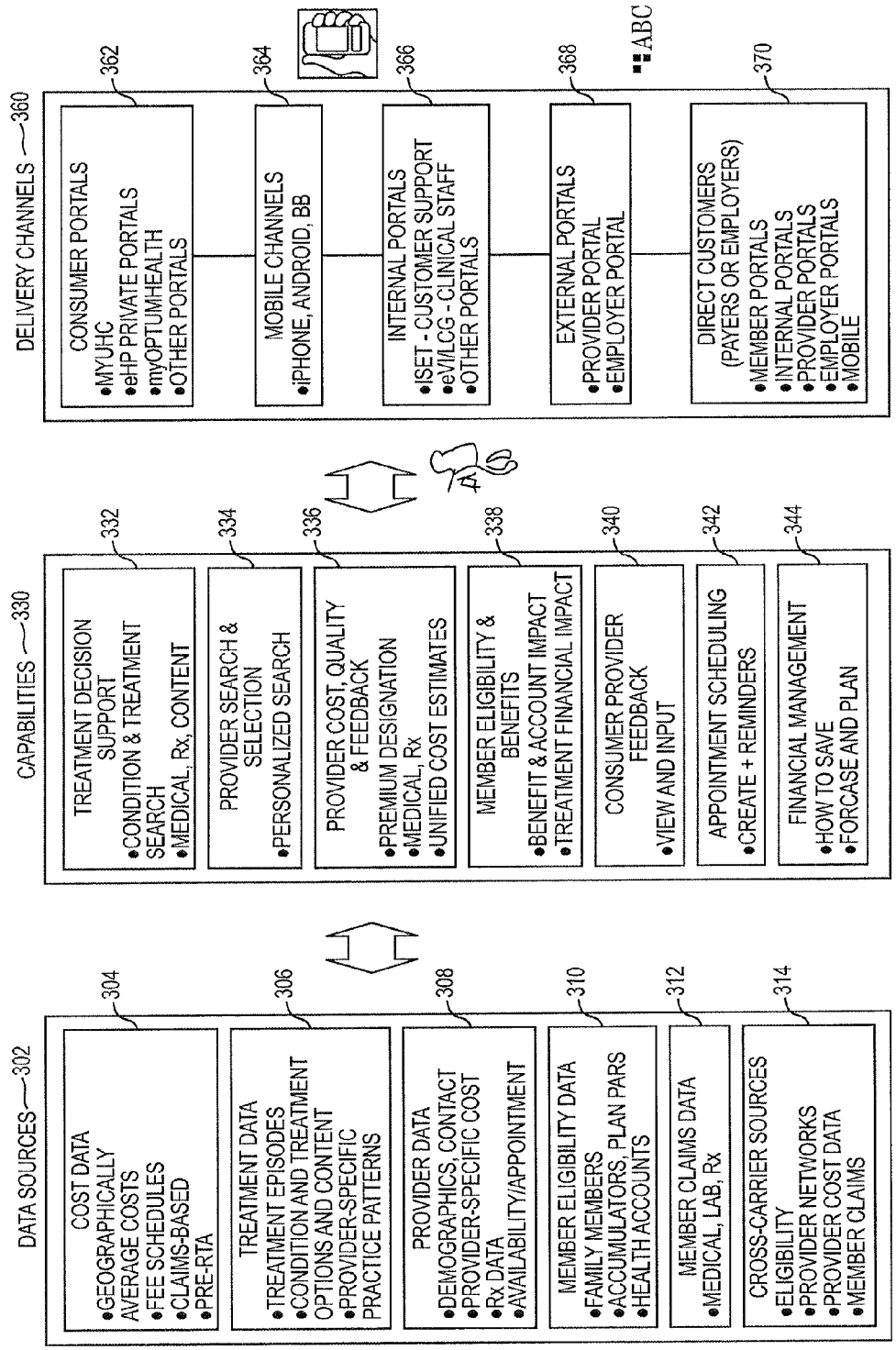
FIG. 3 illustrates data sources and types that may be used to perform capabilities of the present disclosure which may be delivered to a user in accordance with an embodiment of the present disclosure.

Generally, the system 100 of the present disclosure may use various data sources to provide outputs in a variety of different ways. FIG. 3 shows the data sources 302, capabilities 330, and delivery channels 360 that may be included in some embodiments of the present disclosure. As described herein, any useful and appropriate data may be included and used within the systems, methods, and products of the present disclosure. For example data sources 302 may include cost data 304, treatment data 306, provider data 308, member eligibility data 310, member claims data 312, and/or cross-carrier sources 314 for example. Such data may be used in embodiments of the present system to provide certain capabilities 330, for example, but not limited to: treatment decision support 332; provider search and selection 334; provider cost, quality and feedback 336; member eligibility and benefits 338; consumer provider feedback 340; appointment scheduling 342; and/or financial management 344 for example. The user of the systems, methods, and products of the present disclosure may access the capabilities 330 by one or more of the following methods, but are not so limited: via consumer portals 362; mobile channels 364; internal portals 368; and/or direct customers 370 for example.

Figure 4A:
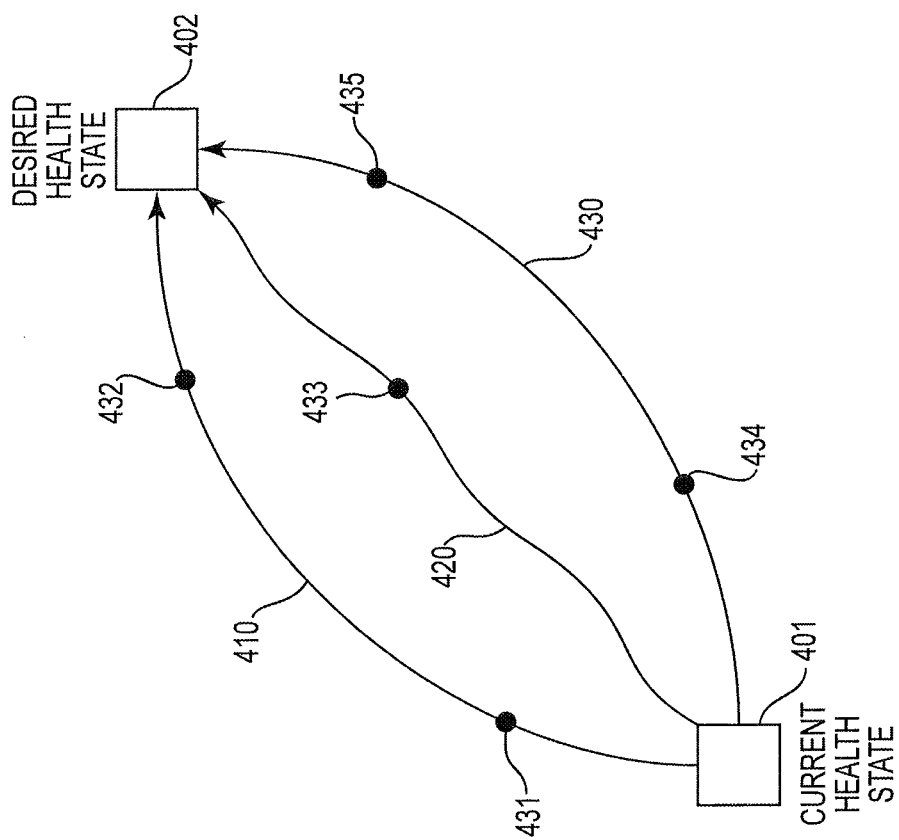
FIG. 4A illustrates an example healthcare path map in accordance with an embodiment of the present disclosure.

Various medical treatment paths, or healthcare paths, will now be discussed with respect to the systems and methods of the present disclosure. An example series of treatment paths is shown in FIG. 4A, which depicts a current health state 401, and a desired health state 402. The healthcare consumer, as shown in this figure, is currently at current health state 401, and is desirous of medical treatment that will bring such consumer to desired health state 402. In order to achieve desired health state 402, one of three, for example, series of treatments is possible, shown in the figure as treatment path 410, treatment path 420, and treatment path 430. As previously discussed, any treatment path may have one or more individual treatments, each having its own costs and potential outcome, and may be available at a plurality of service providers by a plurality of healthcare professionals. For example, as shown in FIG. 4A, treatment path 410 includes individual treatments 431 and 432. Treatment path 420 includes just one treatment 433. Further, treatment path 430 includes individual treatments 434 and 435. FIG. 4A merely provides an example depiction of treatment options, and it will be appreciated that the path from a current health state to a desired health state may include more or fewer than three options, each comprising more or fewer than the number of individual treatments shown.

Figure 4B:
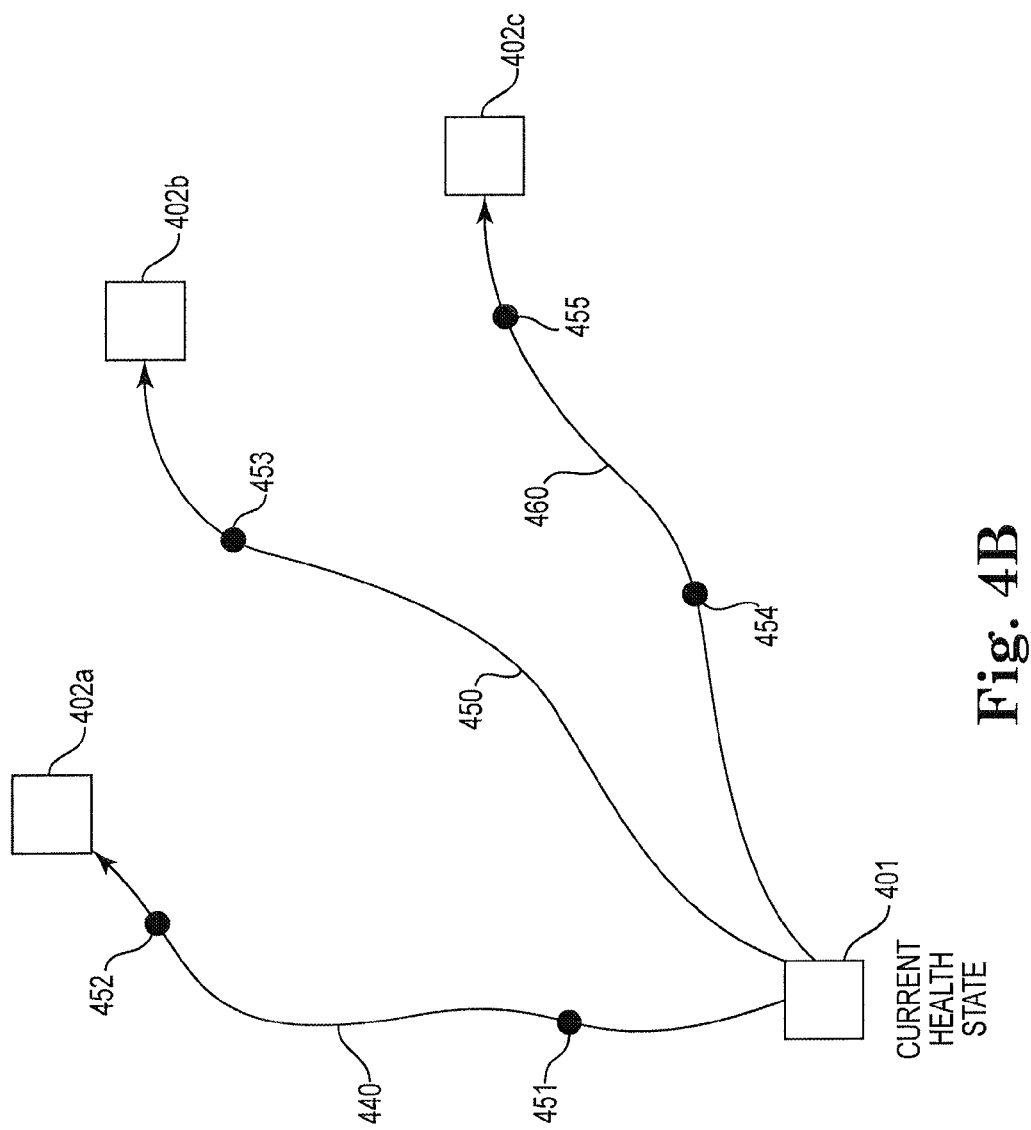
FIG. 4B illustrates another example healthcare path map in accordance with an embodiment of the present disclosure.

In another example, in FIG. 4B, a healthcare consumer having a current health state 401 may have more than one desired health state option. For example, the treatment of a medical condition may result in more than one health outcome, and the healthcare consumer may be desirous of comparing the costs and treatment options to achieve a plurality of healthcare outcomes, i.e., achieving one of the plurality of possible healthcare states. As shown in FIG. 4B, the current health state 401 may result in three possible health outcomes, that is, three healthcare states 402a, 402b, and 402c. The healthcare path 440 from the current state 401 to health state 402a may include treatments 451 and 452. The healthcare path 450 from the current state 401 to health state 402b may include treatments 453. Further, for healthcare path 460, which leads to health state 402c after treatment, may include treatments 454 and 455. Again, FIG. 4B merely provides an example depiction of treatment options, and it will be appreciated that the path from a current health state to a desired health states may include more or fewer than three options, each comprising more or fewer than the number of individual treatments shown.

By providing cost and treatment estimates for a plurality of treatment paths between a given current health state and one or more future or desired health states, the presently described system and method may save healthcare consumers time and money in a fragmented and complex health care system by providing a clear path to follow to meet their health care needs. Further, the presently described system and method allows the healthcare consumer to choose from one or more options, based on treatment outcomes and potential costs, thereby advantageously giving the healthcare consumer a greater freedom of choice in making healthcare decisions.

The aspects of an individual healthcare path will now be described in greater detail. As discussed above, with regard to the various systems and methods for estimating an individual treatment cost, it will be appreciated that any given healthcare path may include a selection from one of a plurality of treatment options, a plurality of treatment facilities, and may be given by a plurality of healthcare professionals. As such, a healthcare path may seek to provide the consumer with recommendations based on cost, availability, and treatment selections, for any given health condition.

Figure 5:
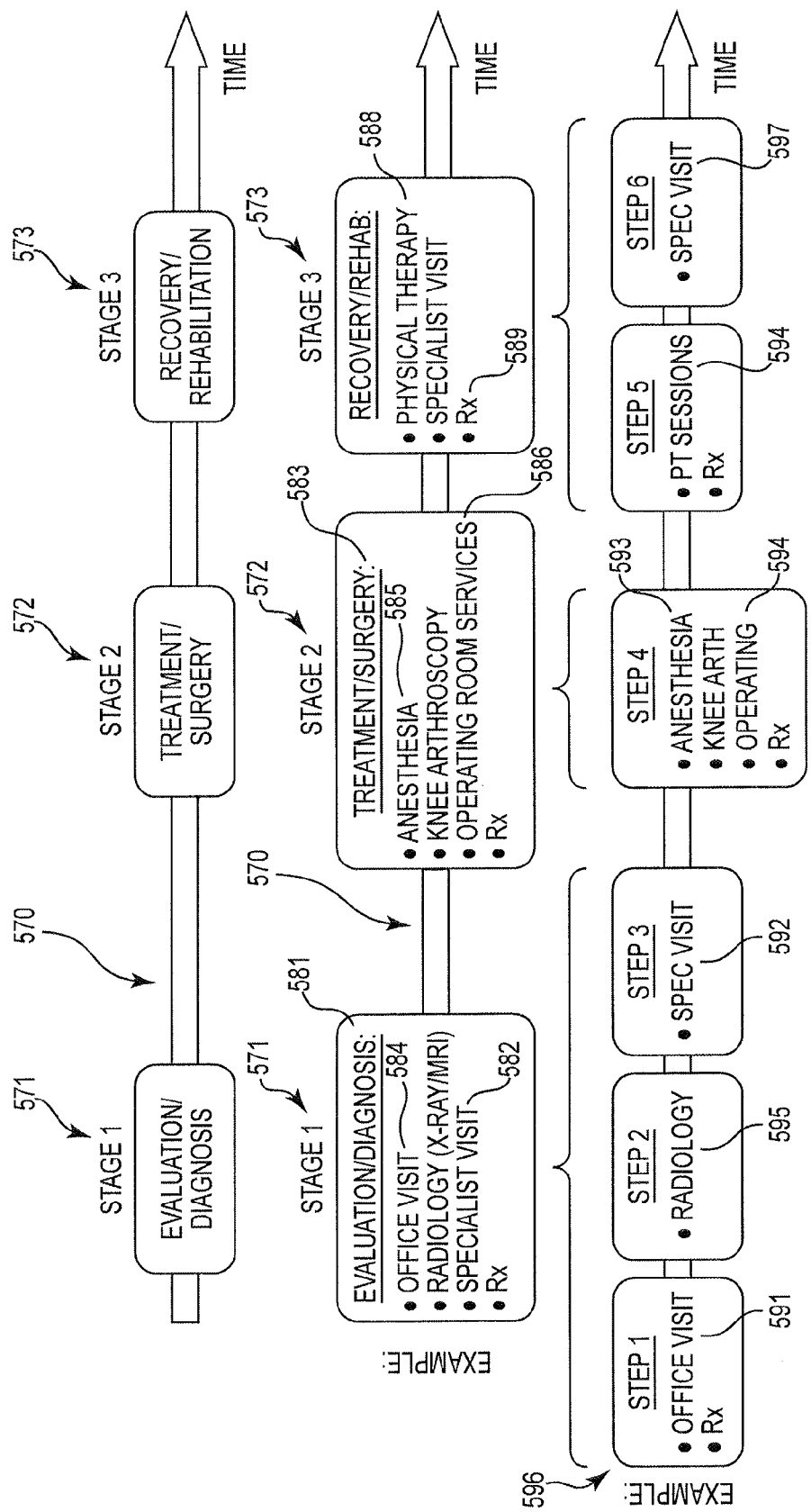
FIG. 5 details aspects of a healthcare path in accordance with an embodiment of the present disclosure.

As shown in greater detail in FIG. 5, a healthcare path 570 may include a plurality of stages. For example, as shown, stages in a healthcare path may include an evaluation/diagnosis stage 571, a treatment/surgery stage 572, and a recovery/rehabilitation stage 573. It will be understood that other or additional stages may also be included in a given healthcare path 570 and are within the spirit and scope of the present disclosure. A stage may include one or more individual aspects, including procedures, treatments, etc. As shown in FIG. 5, stage 1, 571, may be the evaluation or diagnosis 581 stage. Such stage 571 may include, but is not limited to, an office visit 584 or a specialist visit 582, for example. Stage 2, 572, may be a treatment or surgery 583 stage. Such stage may include, for example, among other things, anesthesia 585, and operating room services 586. Further, stage 3, 573, may be a recovery 587 stage, which may include, for example, among other things, physical therapy 588, and a prescription 589. Of course, any given treatment path may include any number of stages, and each such stage may include a plurality of procedures or treatments.

A treatment path such as treatment path 570 shown in FIG. 5 therefore illustrates a complex system of choices that a healthcare consumer makes when deciding on a given treatment option. Further, as discussed above, for a treatment option, there may be a variety of paths to choose from, and a variety of health outcomes to consider. As such, applying the described healthcare cost estimate procedures discussed in the present disclosure to the various treatment paths, including a plurality of treatments, may give the healthcare consumer a better overall picture of the costs, benefits, and results of any given treatment path.

An alternative depiction of a healthcare path is shown at 596, wherein a healthcare path 596 is depicted as a series of steps or healthcare procedures, rather than one or more stages of healthcare. It will be understood that the terminology used herein, including "steps" and "stages" is exemplary only and is not intended to limit embodiments of the present disclosure in any way. As shown, a healthcare path 596 may include a series of steps, which may include an office visit with a prescription 591, a radiology visit 595, a specialist visit 592, anesthesia 593 and surgery 594, physical therapy 594, and a specialist visit 597, in order to complete the course of treatment from a current health state to a desired health state. As may be apparent, the present disclosure is not limited to any particular way of depicting, processing, or providing cost estimates for a healthcare path, and treatments may be grouped into any number of stages, steps, or other like representations, all of which may include one or more cost estimates as described above, in order to give the healthcare consumer the best and/or most user friendly, for example, possible representation of healthcare options so that the healthcare consumer can make the most informed healthcare choice.

Figure 6:
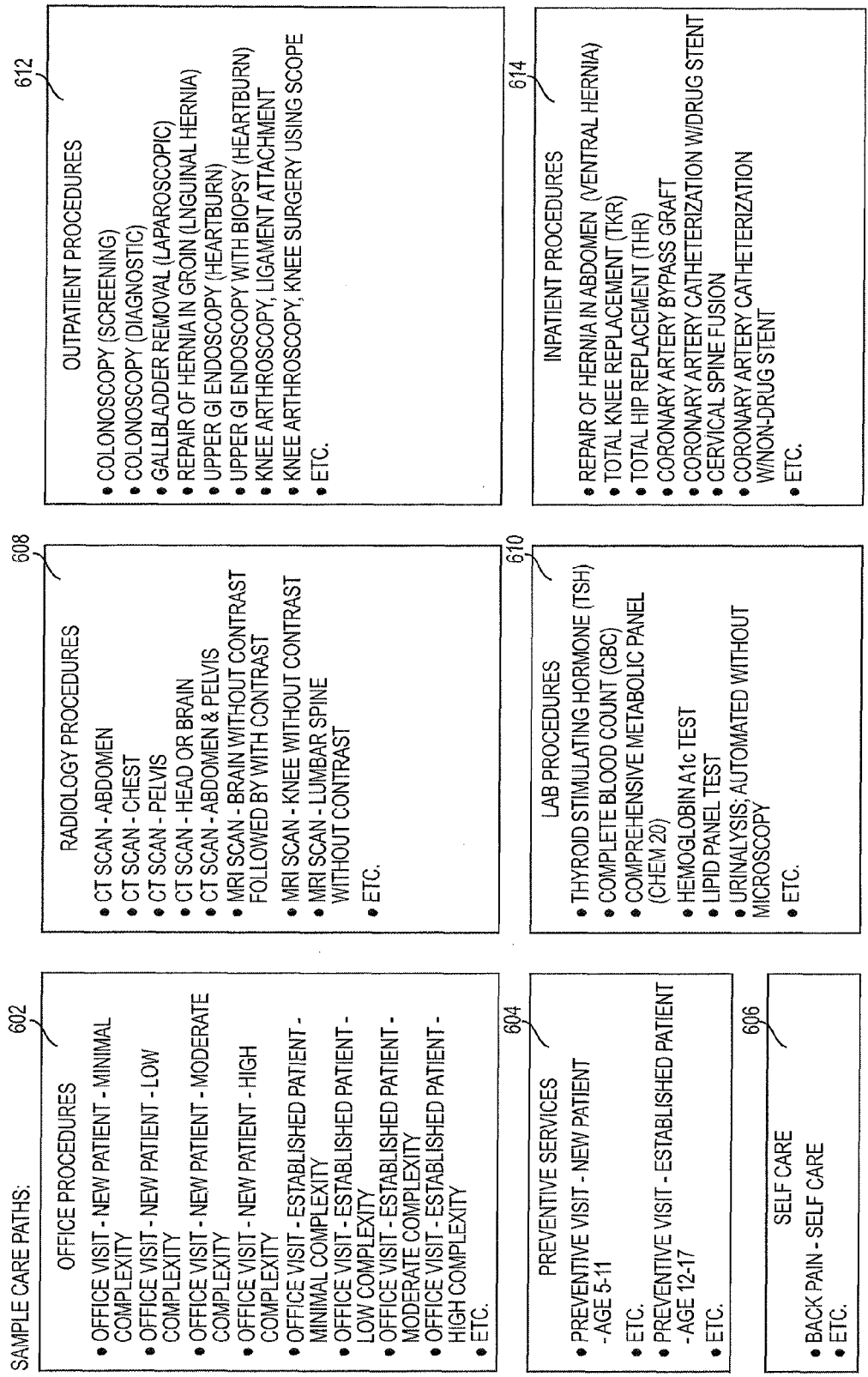
FIG. 6 shows general and specific aspects of a treatment care path in accordance with an embodiment of the present disclosure.

The various steps, stages, treatments, etc. that may be included in a given care path may be defined at varying levels of specificity, according to various embodiments of the present disclosure. As may be appreciated, a certain degree of specificity may be desirable so at to differentiate among meaningfully different steps, treatments, or units in a care path. FIG. 6 shows an example of the level of specificity that may be used in embodiments of the present disclosure, though it will be understood that any useful degree of specificity may be used. Seven different general illustrative categories of treatment are provided in FIG. 6: office procedures 602; preventative services 604; self-care 606; radiology procedures 608; lab procedures 610; outpatient procedures 612; and inpatient procedures 614. Provided below each of the general categories is an exemplary list of more specific procedures that may fall within the general category, and which may be used in conjunction with the systems, methods and products of the present disclosure to generate a more specific and accurate care path analysis for the consumer. For example, radiology procedures 608 may include different types of scans, for example, CT scans and MRI scans. The type of scan performed may be further broken down by the specific area or area(s) that were scanned, for example, a CT scan of the pelvis, or a CT scan of the abdomen and the pelvis.

Within any given stage, step, or other grouping within a healthcare path, each individual procedure, treatment, prescription, or the like may include an individual code. An exemplary process for and description of assigning such codes may be found in U.S. application Ser. No. 10/966,530, filed Oct. 15, 2004, now U.S. Pat. No. 8,005,687, entitled "SYSTEM, METHOD AND COMPUTER PROGRAM PRODUCT FOR ESTIMATING MEDICAL COSTS," which was previously incorporated herein in its entirety. Accordingly, a healthcare path may include a series of one or more healthcare codes indicative of a particular procedure, treatment, prescription, etc. Of course, there may be one, two, or more different options to choose from for any given treatment, and as such, one, two, or more healthcare paths may be provided, with associated codes, for a given course of treatment (see for example FIG. 4A).

It will further be appreciated that a potentially very large number of healthcare paths may be provided to a user to choose from, at least in part because there may be a large number of healthcare facilities from which to choose, each of which may include a large number of healthcare professionals from which to choose, the selection of any one of which may result in a different healthcare path. Thus, in a further aspect of the present disclosure, the systems and methods described herein may use the cost estimate information to select a healthcare path for any given course of treatment that may minimize cost relative to other paths while maintaining high standards of healthcare, which may be generally referred to as a healthcare path optimization procedure.

Figure 7:
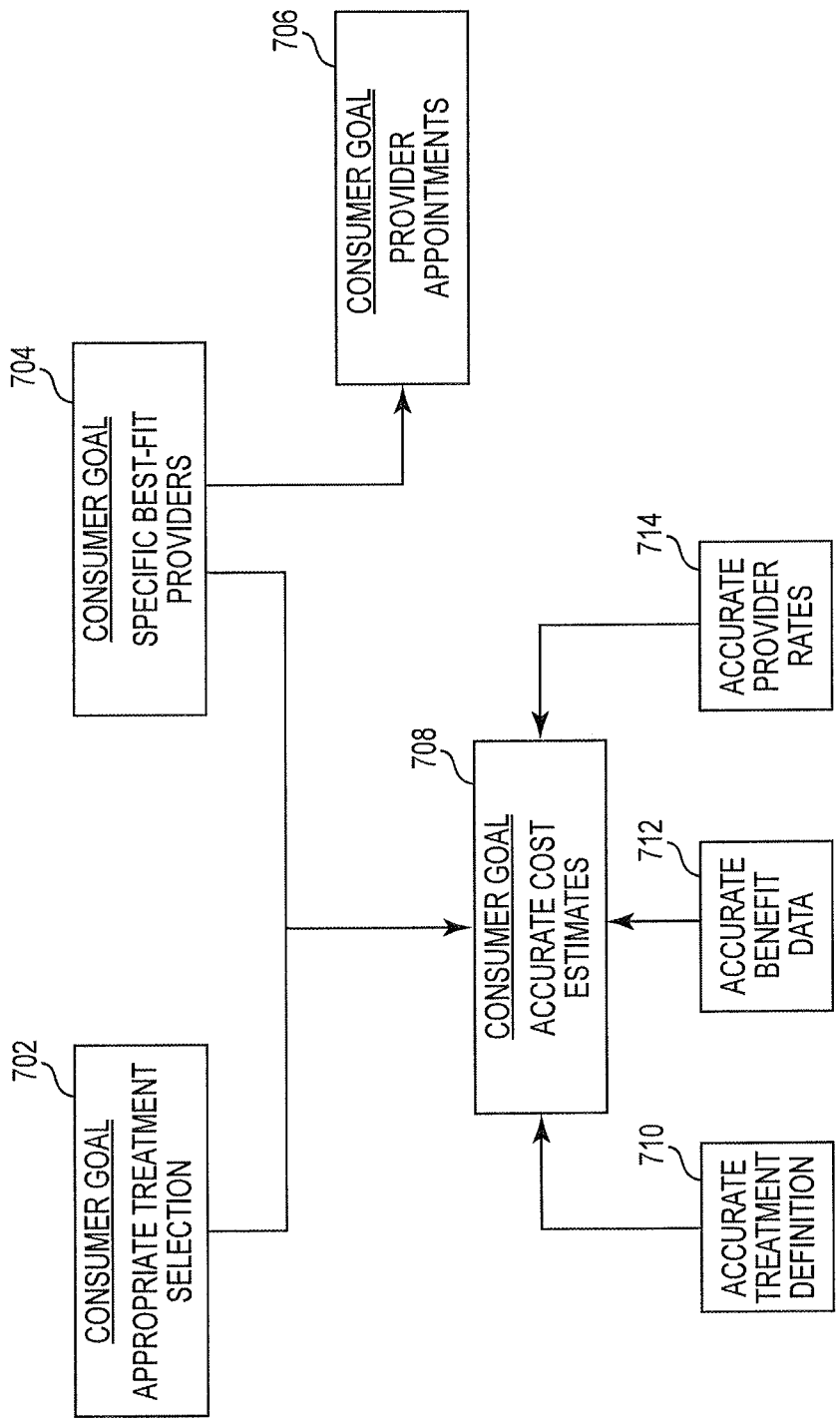
FIGS. 7 and 8 show aspects of systems and methods of the present disclosure related to obtaining accurate cost estimates in accordance with an embodiment of the present disclosure.

FIG. 7 shows a flow chart related to achieving consumer goals using embodiments of the present disclosure. As may be seen, a consumer may have the goal of making an appropriate choice regarding treatment selection 702. In order for embodiments of the present disclosure to facilitate that consumer goal, the system may include data related to the condition of the consumer as well as treatment options for the condition, and the system may also provide treatment decision support to the consumer, among other things. In some cases, a consumer may or may also have the goal of choosing the best provider(s) for a particular treatment 704. Embodiments of the present disclosure may include using provider demographics, provider cost, quality, and outcomes data, consumer feedback, and/or other sources of information to facilitate a consumer goal of choosing the best provider for a particular treatment 704. Along with a goal of choosing an optimum provider, a consumer may have a goal related to making provider appointments 706. Embodiments of the present disclosure may include accessing data related to provider availability, provider connectivity, and what should be done in preparation for an office visit, for example in order to facilitate meeting the consumer goal of optimizing provider appointments 706.

In addition to the goals discussed above, a consumer may have the goal of obtaining an accurate cost estimate 708 for on or more selection the consumer has made related to one or more of their treatment goals 702 and/or 704. As discussed and incorporated by reference herein, embodiments of the present disclosure make use of multiple sources of information to provide a consumer with accurate cost estimates for various treatments. In some embodiments, the systems and methods of the present disclosure may include ensuring that the treatment definition 710 identified is accurate. Ensuring the accuracy of the treatment definition 710 may involve accessing and incorporating provider-specific treatment episode data, including more treatment options, and/or other alternatives. Systems and methods of the present disclosure may also include using accurate benefit data 712 to provide accurate cost estimates 708. Accurate benefit data may be generated by reviewing and incorporating current health account data, eligibility parameters, and/or other relevant information. Further, systems and methods of the present disclosure may include using accurate provider rates 714 to help provide accurate cost estimates 708. Accurate provider rates may be obtained in some cases by consulting fee schedules, claims-based rates, geographical average rates, and/or any other relevant or desirable source.

Figure 8:
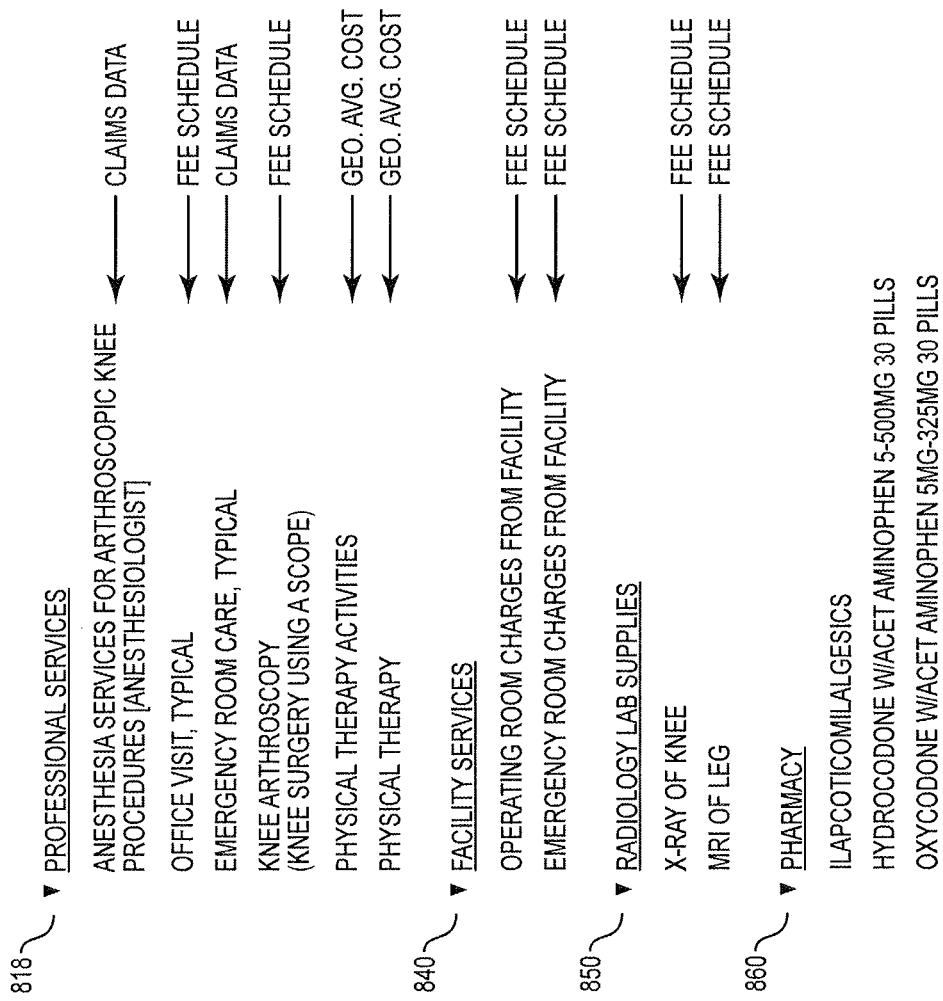

FIG. 8 provides an example of various data that may be used or used in part to provide accurate cost estimates to the consumer. For example, professional services 718 may be broken down into a variety of different therapies and/or procedures. Depending on the therapy or procedure, one or more sources of data may be consulted and used to determine an accurate cost estimate for that therapy or procedure. For example, as shown, claims data may be used as a source of data to determine the cost estimate for anesthesia services for arthroscopic knee procedures. Similarly, geographical average cost may be used as a source of data to determine the cost estimate for physical therapy activities or physical therapy. In the same manner, facility services 840, radiology/lab/supplies 850, and pharmacy services 860 may include procedures and/or treatments for which cost estimates may be provided by consulting and utilizing data from one or more available source. In some embodiments, the sources of available data may be provided largely by one source, for example, a large health care company that may have access to a significant amount of patient/member data and claims data. In other embodiments, however, the source of data may use or may also use data, for example claims data and/or member data, from other parties, companies, and/or entities, as desirable. The systems and methods of the present disclosure may be customizable to include any desirable sources of data.

Figure 9A:
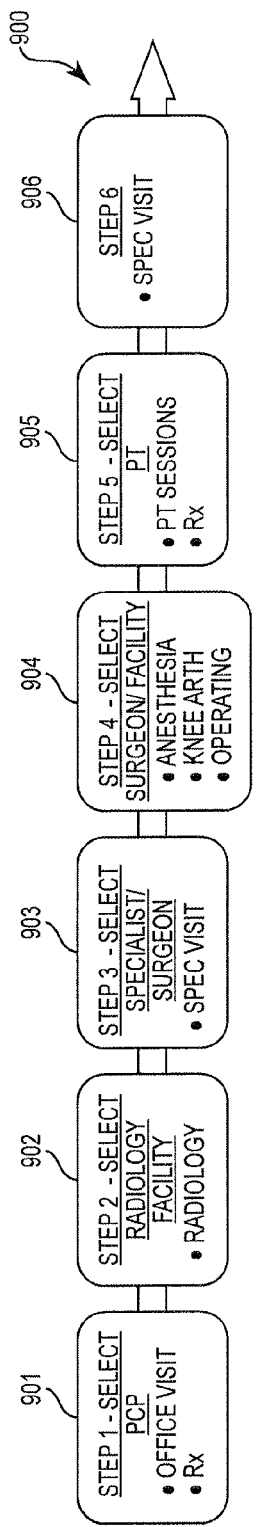
FIGS. 9A and 9B illustrate an optimization procedure among various healthcare options within a healthcare path in accordance with an embodiment of the present disclosure.

FIG. 9A depicts an example healthcare path 900, including six steps. With respect to each step, a treatment, healthcare facility, and healthcare professional may be selected from a plurality of choices. Thus, for example, at step 1, 901, a preventive care provider is selected, which may result in an office visit and/or a prescription, among other things. At step 2, 902, a radiology procedure may be selected, wherein a particular radiological facility and provider may be selected. At step 3, 903, a specialist may be required in the course of treatment, and as such, a facility and provider, for example a surgeon, may be selected. At step 4, 904, the actual surgery may take place, including a selection of surgeries, anesthesia, operating procedures, etc. At step 5, 905, post surgery procedures may occur, where a selection may be made from a variety of outpatient therapies, offered by a plurality of providers, and one or more prescriptions may be selected. Further, at step 6, 906, a follow-up specialist visit may be required, and a selection therefore may be made. As is apparent, this single healthcare path may include a wide variety of choices of treatment options, healthcare facilities, healthcare providers, and other choices, such that even figuring out the best cost and option from this single path would be prohibitive without healthcare path optimization procedures. It can thus be difficult for the average healthcare consumer to make an intelligent and fully informed decision to select the best and most cost effective treatment.

Figure 9B:
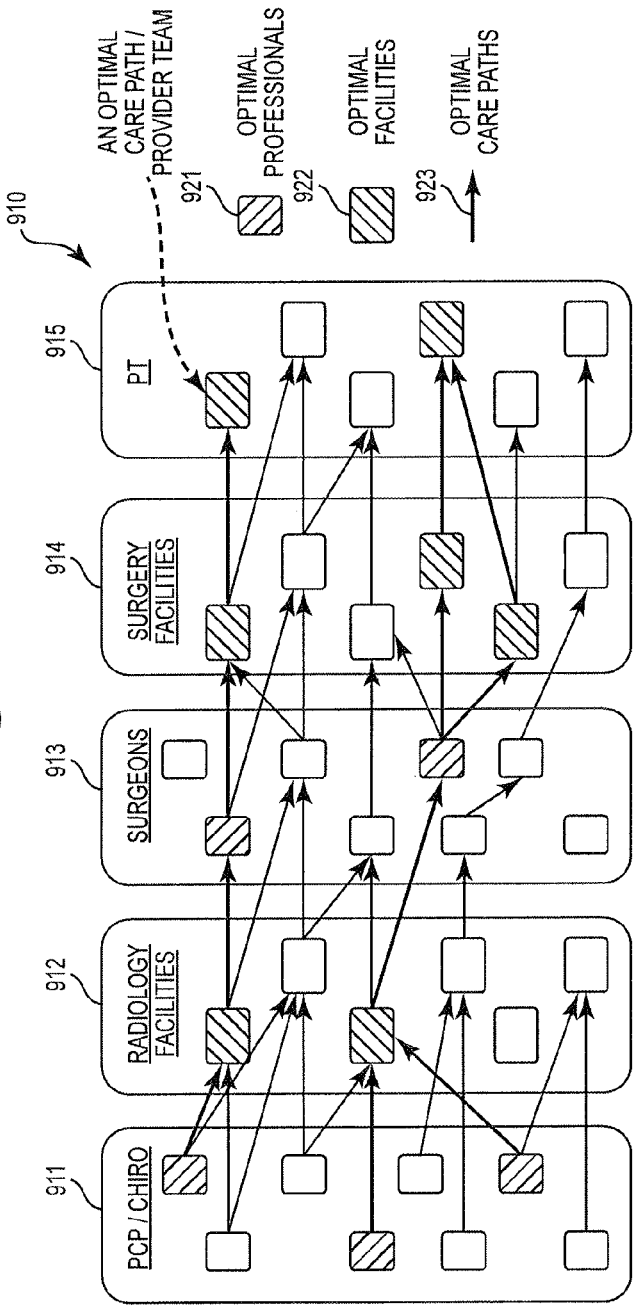

As such, FIG. 9B depicts an example healthcare path optimization procedure in connection with the healthcare path shown in FIG. 9A. Steps 901 through 905 correspond with selections 911 through 915, respectively. Based on the information made available through the systems and methods of cost estimation discussed above, professionals that have been found to perform high quality care at relatively low cost, or "optimal professionals" 921 and facilities that have been found to perform high quality care at relatively low cost, or "optimal facilities" 922 may be selected as shown. For example, at selection 911, three optimal preventive care providers are available. Further, at selection 912, two optimal radiological facilities are available. Similar availabilities are shown with respect to surgeons, surgery facilities, and physical therapy (913-915). As such, the wide variety of options is reduced down to a handful of optimal care paths 923 (bold arrows), which may be provided to the healthcare consumer for selection thereamong. These care paths reflect professional referral patterns and consumer usage patterns. Based on these paths, an optimal path is defined.

FIGS. 9A and 9B depict the contrast between a user selected care path (FIG. 9A), where information related thereto may simply be provided to the user, and a system optimized care path (FIG. 9B), wherein the system uses medical cost data, as discussed above, to provide the consumer with an optimum care path (as is indicated by the darker arrows in FIG. 9B). As such, where an optimization schedule is provided, the consumer may be incentivized to select the most advantageous care path, as determined by the system.

As will be appreciated, the terms "optimizing" and "optimal" and the like are indicative of relative performance. As discussed above, the cost estimation can be performed with respect to procedures, facilities, professionals, etc., where the costs incurred can be wide ranging. Thus, optimization seeks to determine one or more such procedures, facilities, and professionals that provide high-quality care as determined by outcomes, while maintaining relatively lower costs. FIG. 9B shows examples thereof.

It will be further appreciated that, in one aspect of the disclosure, consumers are incentivized or otherwise encouraged to choose optimal providers, given the available data. Such providers may be referred to as "Tier 1." Similarly, consumers are disincentivized or otherwise discouraged from using less optimal providers, given the available data. Such providers may be referred to as "Tier 2." As such, in one aspect, consumers are incentivized to shift their health care decisions from Tier 2 providers to Tier 1 providers. The example Tiers used herein are given for illustrative purposes only, and it will be appreciated that more or fewer aspects of a like hierarchy are included within the scope of the present disclosure.

The results of an optimization in accordance with the present disclosure may be displayed to the healthcare consumer in any of a variety of methods. For example, a healthcare path or series of paths as shown for example in FIGS. 4A and 4B may be presented to the consumer in electronic form, for example, using a computer connected to the Internet or other network, wherein the information may be provided to the consumer using an Internet Web address, email, or other electronic form. Alternatively, the results of an optimization may be provided to the consumer in physical form, such as on paper and delivered through the mail. Other known forms of depiction and other methods of delivery to the healthcare consumer are considered to be within the scope of this disclosure.

Figure 10:
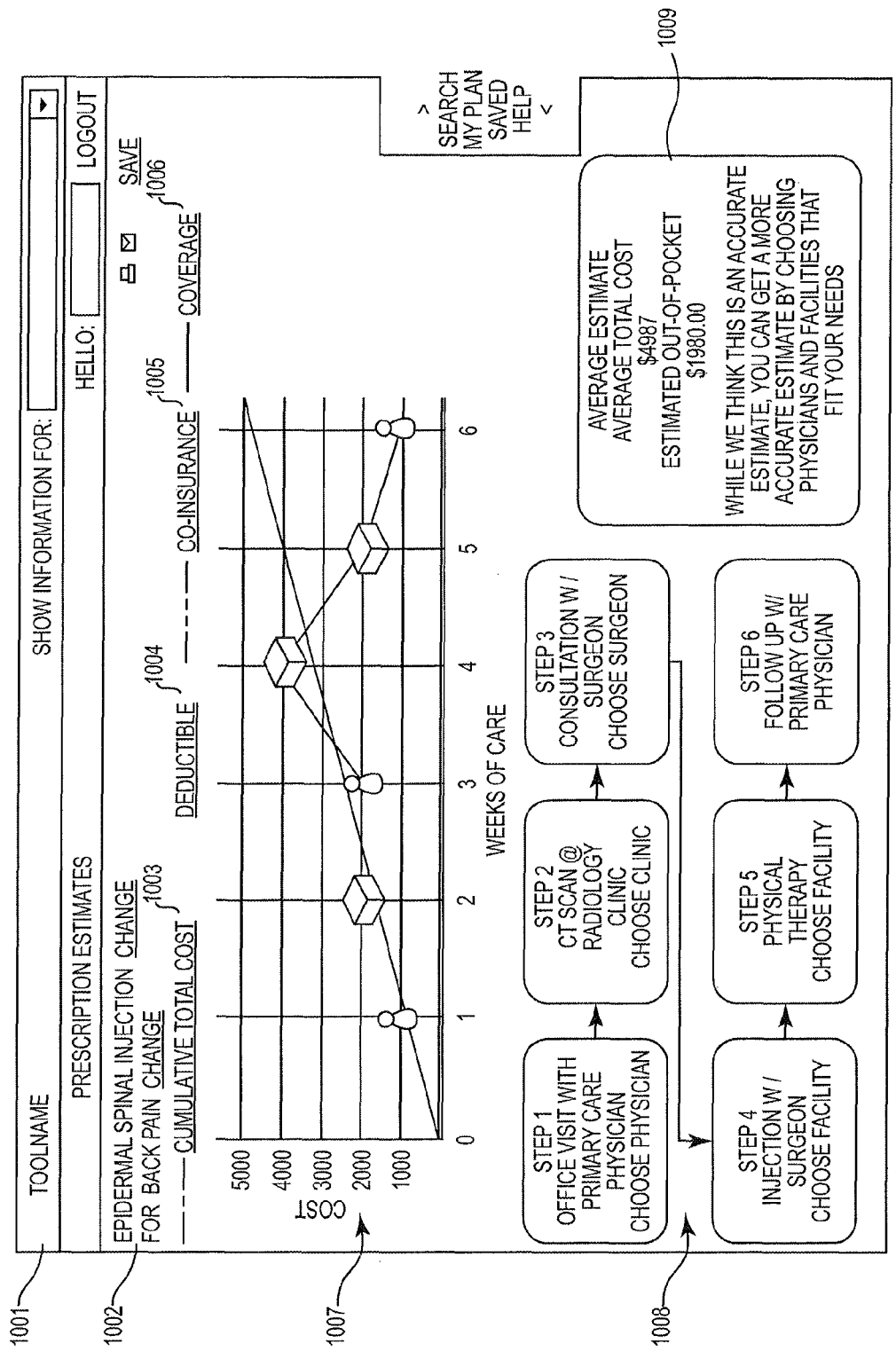
FIG. 10 illustrates an example healthcare path display in accordance with an embodiment of the present disclosure.

An example optimization result is depicted, in one embodiment, in FIG. 10, for provision to the healthcare consumer. The depiction may include an information bar 1001, which may include the name of the depiction, the consumer name, and an estimate designation. As further shown in FIG. 10, the course of treatment 1002 is depicted for the consumer's reference. With regard to the cost estimates of the particular healthcare path shown, the estimate may be provided in graphical form 1007, and may include an estimate of costs that are deductible 1004, co-insurance 1005, and/or covered 1006, and may also include a cumulative total cost 1003 thereof. The estimate of costs may be provided over the time range of treatments, which may include a number of weeks of care, and when such costs may be incurred. The depiction, as shown in FIG. 10, may also include a stepwise illustration of the healthcare path, including for example steps 1 through 6. This may correspond to the depiction as shown in, for example, FIG. 5. Further, a summary of the cost estimate may be provided, as shown at block 1009.

Figure 11A:
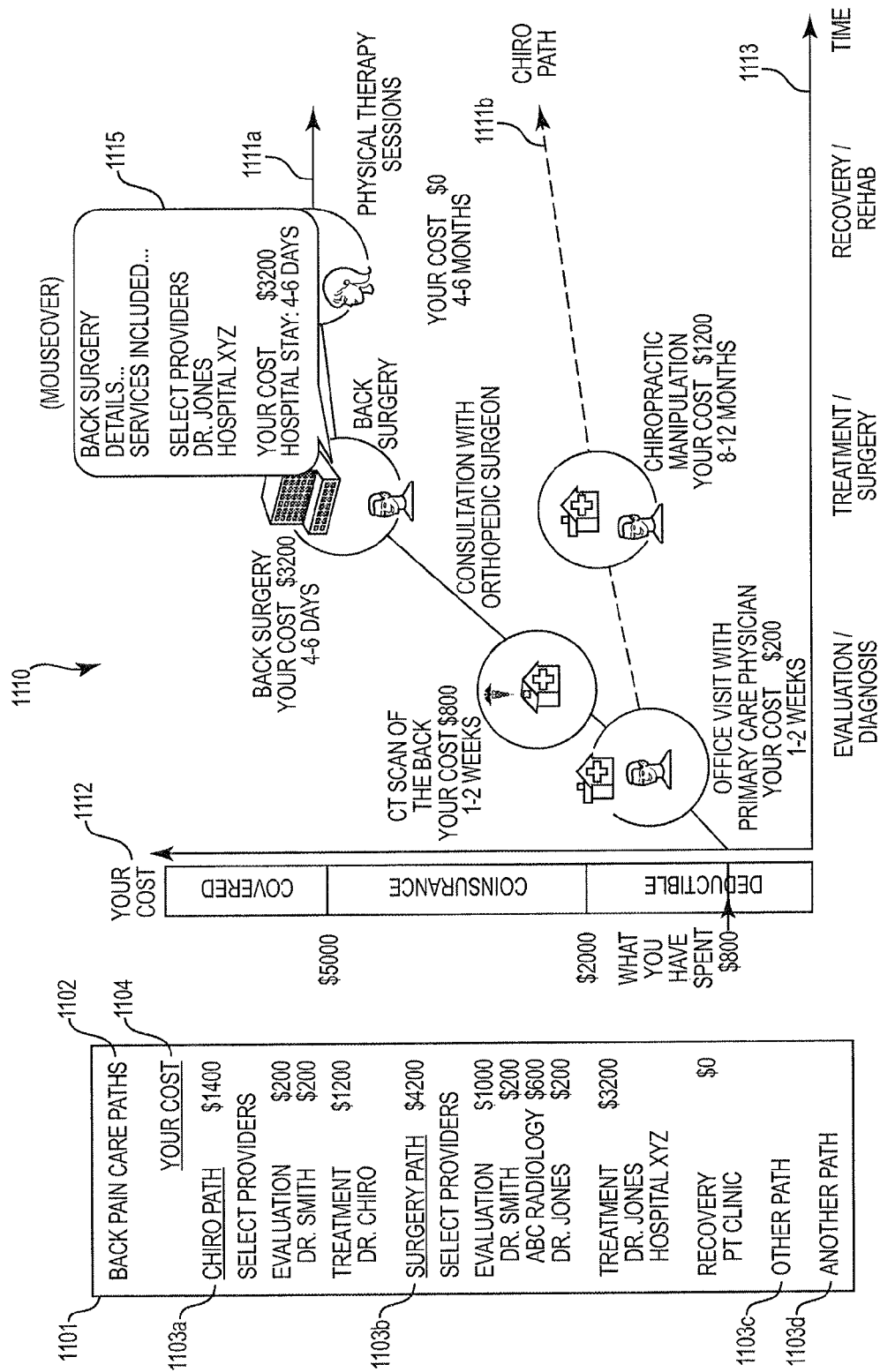
FIG. 11A illustrates another example healthcare path display in accordance with an embodiment of the present disclosure.
Figure 11B:
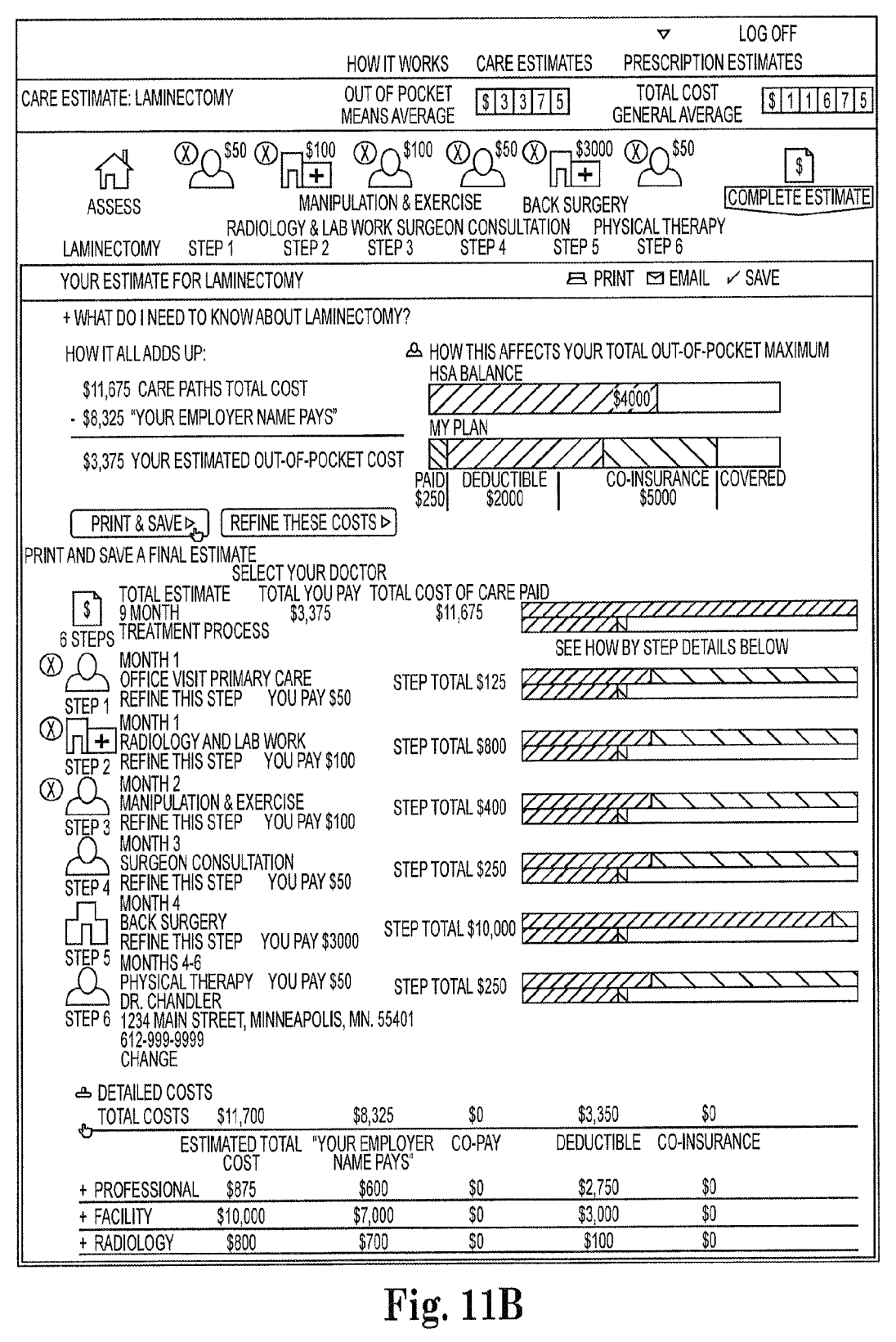

In another embodiment, an alternative depiction of a healthcare path may be provided, as shown in FIG. 11A. For example, as shown in FIG. 11A, a block 1101 of possible healthcare paths may be depicted, along with their associated costs. Shown in block 1101 are healthcare paths 1103a through 1103d. Path 1103a is a chiropractic path, which may include evaluation and treatment by one or more providers. Path 1103b is a surgery path, which may include evaluation, treatment, and recovery time. Paths 1103c and 1103d are shown for illustration, but left blank for ease of illustration. With respect to each path, a total cost of treatment is shown, 1104. As is apparent, the chiropractic path 1103a, at $1400, is considerably less expensive than the surgery path 1103b, at $4200. For the purposes of further illustration, a chart 1110 is further provided to the healthcare consumer in order to depict certain aspects of each healthcare path available. For example, chart 1110 may include a representation of costs 1112, which may include those that are deductible, co-insurance, and/or covered. The chart may also include a timeline for each path, including evaluation and diagnosis, treatment and surgery, and/or recovery and rehab time. Each path may be shown as a series of steps over time, with associated costs. As shown in FIG. 11, path 1111a is the surgery path and includes the office visit, consultation, surgery, and physical therapy, with associated costs. Alternatively, path 1111b shows the chiropractic path, including an office visit, and a chiropractic procedure, including the associated costs and timeline. In some embodiments, the healthcare consumer may be able to "mouse over" a particular step in the chart, and gain further information about the details of the step, the services included, the providers available, the facilities available, the cost, the time for the procedure, and/or other information. FIG. 11B shows an example of how a user of the products, methods and systems of the present disclosure may be provided information related to a particular care path. Similarly FIG. 11C shows an example of how a user of the products, methods and systems of the present disclosure may be provided information related to selecting a particular provider.

It will be appreciated that the healthcare path and cost estimates shown in FIGS. 10 and 11A and B are merely examples, and such depictions may include more or fewer paths, more or fewer treatment options, and other information associated with the treatment of a health condition as has generally been described herein.

In a further aspect of the present disclosure, it will be appreciated that there is a large number of courses of treatment for health conditions that are routinely provided to healthcare consumers. Such procedures may be referred to as "high-volume" or "commodity" procedures, wherein there are a large number of healthcare providers and healthcare facilities providing such services. As described above with respect to cost estimation, the range of costs for such common procedures can vary widely. As such, it may be desirable to establish a "preferred," or series of preferred, healthcare paths from which to choose for such common procedures. For example, a common procedure that is routinely done is an appendectomy. The procedures for the treatment of a ruptured appendix are and have been well known for years, and is a routine surgery performed by most hospitals and by most general practice surgeons. As such, when a patient requires this type of treatment, it may be desirable to have a preferred healthcare path set forth for the consumer to choose. In this manner, the common procedures and healthcare treatments that healthcare consumers are most likely to request will be readily available to the healthcare consumer without the need to perform new cost estimation computations and optimizations each time such inquiry is made.

Figure 12:
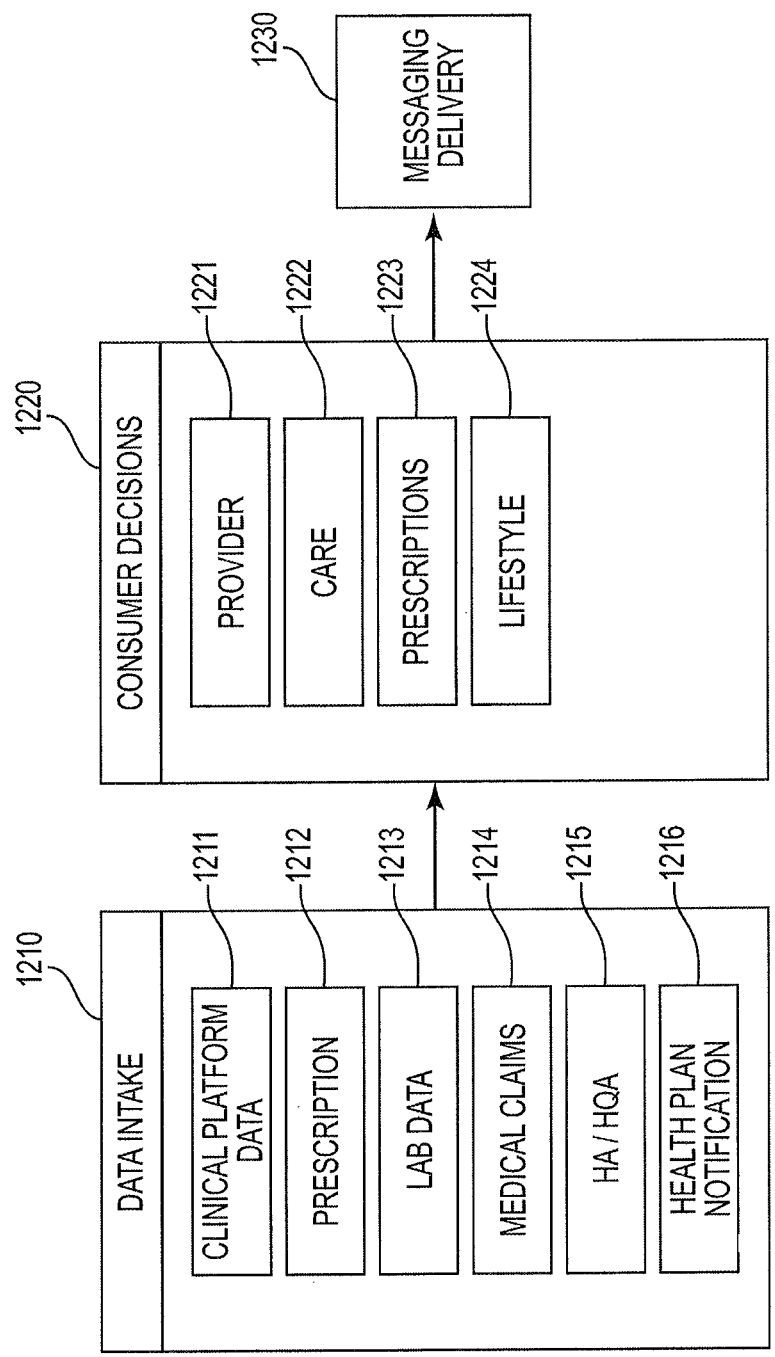
FIG. 12 illustrates an electronic advice module in accordance with the present disclosure.

In a further aspect of the present disclosure, FIG. 12 illustrates an embodiment of an electronic advice module. The electronic advice module may be provided so as to provide consumers with advice about various aspects of their medical care, personal health, and overall well-being. As shown in FIG. 12, a data intake component 1210 receives electronic data, including clinical platform data 1211, prescription data, 1212, lab data 1213, medical claims data 1214, health assessment/health quality assessment data, and health plan notification data regarding a consumer. This information is segregated into various health-related aspects as shown at the consumer decisions component 1220, which may include provider aspects 1221, care aspects 1222, prescription aspects 1223, and lifestyle aspects 1224. This information may be used to provide consumers with relevant information through a messaging system 1230.

Figure 13:
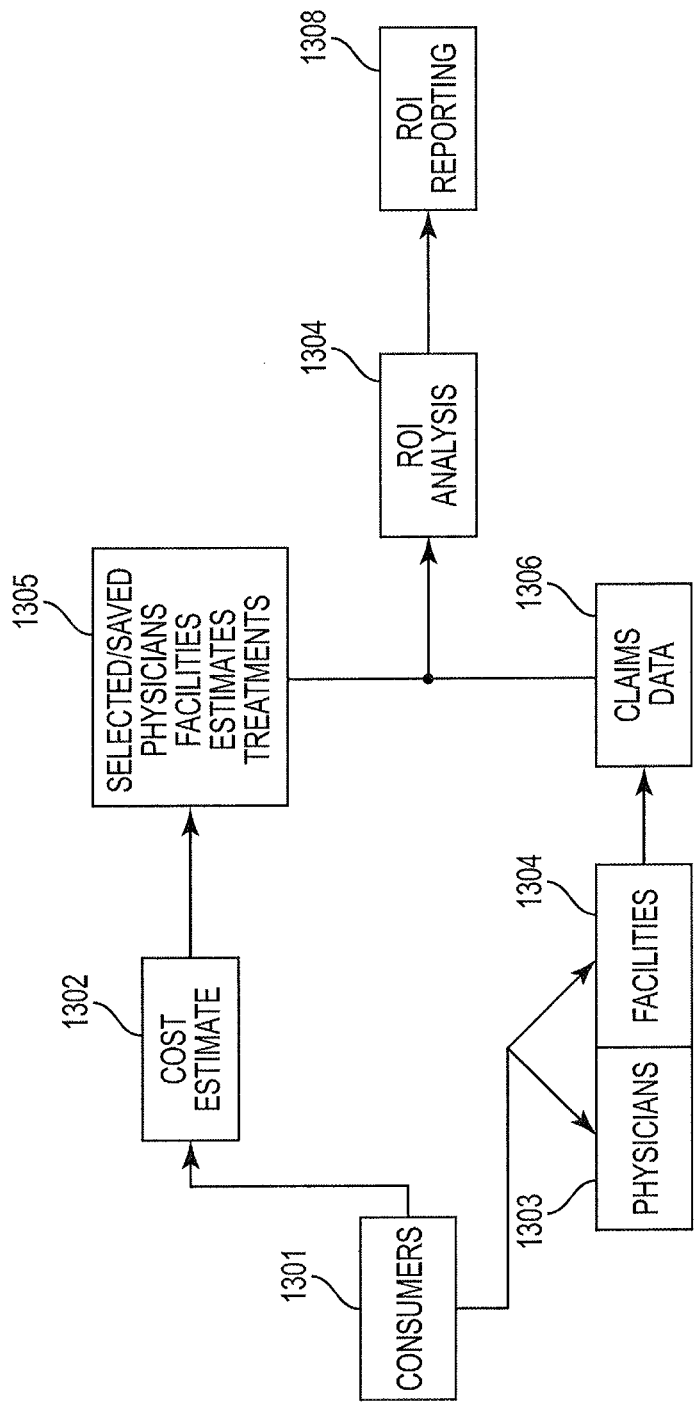
FIG. 13 illustrates a return on investment module in accordance with the present disclosure

In a further aspect of the present disclosure, FIG. 13 illustrates an embodiment of a return on investment (ROI) measurement and tracking module. Consumer data 1301 is received into a cost estimator (as described above) 1302. Selected/saved data regarding physicians, facilities, estimates, and treatments 1305 may be used as well. The consumers choose physicians 1303 and facilities 1304, and a medical cost is incurred, shown in the form of claims data 1306. Medical cost data resulting from 1302/1305 may be compared against actual data from the claims 1306. An ROI analysis is performed 1307, for example, by comparing the actual cost to a baseline cost from the data 1302/1305. Various reports 1308 may be generated from an ROI analysis 1307, as will be known to those of ordinary skill in the art.

Figure 14:
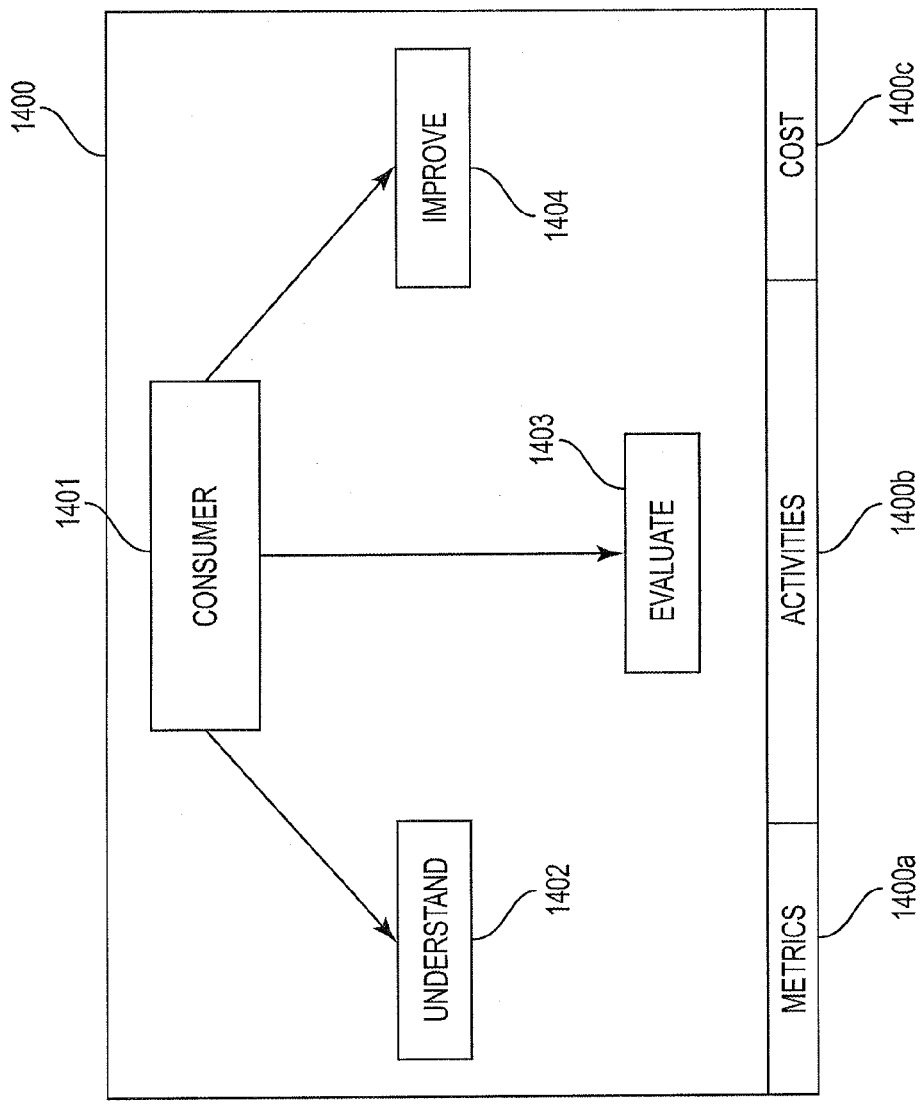
FIG. 14 illustrates an electronic consumer report card in accordance with the present disclosure.

In a further aspect of the present disclosure shown in FIG. 14, a consumer report card 1400 may be provided, concerning consumer health metrics 1400a, consumer health activity metrics 1400b, and consumer medical cost metrics 1400c. The report card 1400 may be provided to consumers 1401 based on medical claims information processed regarding the consumer, and based on personal information supplied by the consumer, for example, through a health assessment. A report card 1400 may include information to help the consumer "understand" 1402 the health care information that has been provided to them. A report card 1400 may include information to help the consumer "evaluate" 1403 the health care information that has been provided to them. A report card 1400 may include information to help the consumer "improve" 1404 a health condition. Health care information to be provided may result from a recent care episode, a period recurring evaluation, or health assessment information, for example. FIGS. 12 through 14 show how the consumer may select the right provider, right care path, right prescriptions, and right lifestyle. The information allows the system to suggest to the consumer a more cost effective option without sacrificing quality. For instance, if a user is using a high cost provider, the system may suggest other providers from which the consumer may select a more cost effective option with similar quality and/or similar outcome.

The benefits of the presently disclosed system and method, including the healthcare path approach coupled with cost estimation, may include a more clear, concise, and easy to understand depiction of the healthcare options that are available to consumers for the treatment of any given medical condition. Using the systems and methods described herein, the consumer may be able to enter a health condition, and receive one or more optional healthcare paths that have been optimized for the healthcare consumer based on the cost estimation and path optimization techniques described herein. Further, the system and methods described herein may provide the healthcare treatment options to the consumer in an easy-to-read and understand format, such as a graphical format or chart display showing the length of time for the total course of treatment, the associated costs, and/or other information. Further, for common procedures, one or more preferred healthcare paths may be provided to the consumer for easier selection. As such, the complex and fragmented world of healthcare options is brought into a more manageable form for the consumer to make the best healthcare decision possible.

While the methods disclosed herein have been described and shown with reference to particular operations performed in a particular order, it will be understood that these operations may be combined, sub-divided, or re-ordered to form equivalent methods without departing from the teachings of the present invention. Accordingly, unless specifically indicated herein, the order and grouping of the operations is not a limitation of the present invention.

It should be appreciated that reference throughout this specification to "one embodiment" or "an embodiment" or "one example" or "an example" means that a particular feature, structure or characteristic described in connection with the embodiment may be included in at least one embodiment of the present invention. Therefore, it should be appreciated that two or more references to "an embodiment" or "one embodiment" or "an alternative embodiment" or "one example" and "an example" in various portions of this specification are not necessarily all referring to the same embodiment. Furthermore, the particular features, structures or characteristics may be combined as desired in one or more embodiments of the invention.

Similarly, it should be appreciated that in the foregoing description of example embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed inventions require more features than are expressly recited in each claim. Rather, as the following claims reflect, inventive aspects lie in less than all features of a single foregoing disclosed embodiment, and each embodiment described herein may contain more than one inventive feature.

While the invention has been particularly shown and described with reference to embodiments thereof, it will be understood by those skilled in the art that various other changes in the form and details may be made without departing from the spirit and scope of the invention.

What is claimed is:

1. A computer implemented method for selecting a treatment care path, comprising:
    receiving, by the computer, identification of a health condition and a selection of at least one desired medical outcome after treatment of the health condition;
    identifying, by the computer, one or more treatment care paths, each comprising a plurality of steps over a time range to achieve the selected at least one desired medical outcome, wherein at least one step within the plurality of steps comprises at least one medical service or treatment to achieve the desired medical outcome;
    for each of the at least one medical service or treatment in the one or more treatment care paths, identifying, by the computer, one or more providers offering the medical service or treatment;
    for each of the one or more providers, providing a cost estimate for receiving the medical service or treatment;
    optimizing, by the computer, the one or more treatment care paths at least based on ranking providers offering the at least one medical service or treatment within each of the one or more treatment care paths, wherein the providers are ranked from lowest provider cost estimate to highest provider cost estimate;
    determining, by the computer, an estimated cumulative total cost for the optimized one or more treatment care paths, the estimated cumulative total cost comprising an estimated cost to the consumer and an estimated cost to an insurance provider;
    determining, by the computer, at least estimated consumer costs for individual steps in the plurality of steps within each of the optimized one or more treatment care paths;
    identifying, by the computer, where within the time range the estimated consumer costs for the individual steps will be incurred within each of the optimized one or more treatment care paths; and
    providing for display, by the computer, an indication of where the estimated consumer costs will be incurred within the time range.

2. The method of claim 1, the one or more treatment care paths having the same desired medical outcome.

3. The method of claim 1, the one or more treatment care paths having at least two different desired medical outcomes.

4. The method of claim 1, further comprising providing for display information related to a quality of the one or more providers, the quality of the one or more providers based on quality assessment data.

5. The method of claim 4, wherein the step of optimizing, is further based on the quality of the one or more providers.

6. The method of claim 1, wherein the at least one medical service or treatment comprises an office visit, receiving a prescription for medication, a radiology appointment, or surgery.

7. The method of claim 1, wherein in the one or more providers comprise one or more of a medical facility or a medical professional.

8. The method of claim 1, wherein the cost estimate is provided by:
   determining, by the computer, whether the medical service or treatment is within a fee schedule of the provider, and if so, providing the cost estimate based thereon;
   where the fee schedule is unavailable, determining, by the computer, whether the medical service or treatment corresponds to prior claims data for the medical service or treatment administered by the provider, and if so, providing the cost estimate based thereon; or
   where the prior claims data is unavailable for the medical service or treatment offered by the provider, determining, by the computer, the cost estimate based on a geographic average for the medical service or treatment.

9. The method of claim 1, further comprising providing for display, by the computer, at least one of the optimized one or more treatment care paths, the aggregated cumulative total costs, or the estimated consumer costs for the individual steps.

10. A system to generate at least one medical treatment care path in response to receiving a health condition and at least one medical outcome after treatment of the health condition, comprising:
    a computer processor configured to execute instructions to:
    receive identification of a health condition and a selection of at least one desired medical outcome after treatment of the health condition;
    identify one or more treatment care paths, each comprising a plurality of steps over a time range to achieve the selected at least one desired medical outcome, wherein at least one step within the plurality of steps comprises at least one medical service or treatment to achieve the desired medical outcome;
    for each of the at least one medical service or treatment in the one or more treatment care paths, identify one or more providers offering the medical service or treatment;
    for each of the one or more providers, provide a cost estimate for receiving the medical service or treatment;
    optimize the one or more treatment care paths at least based on ranking providers offering the at least one medical service or treatment within each of the one or more treatment care paths, wherein the providers are ranked from lowest provider cost estimate to highest provider cost estimate;
    determine an estimated cumulative total cost for the optimized one or more treatment care paths, the estimated cumulative total cost comprising an estimated cost to the consumer and an estimated cost to an insurance provider;
    determine at least estimated consumer costs for individual steps in the plurality of steps within each of the optimized one or more treatment care paths;
    identify where within the time range the estimated consumer costs for the individual steps will be incurred within each of the optimized one or more treatment care paths; and
    provide for display an indication of where the estimated consumer costs will be incurred within the time range.

11. The system of claim 10, wherein the computer processor is further configured to provide for display information related to a quality of the one or more providers available to perform the at least one medical service or treatment, the quality of the one or more providers based on quality assessment data.

12. The system of claim 10, wherein in the one or more providers comprises one or more of a medical facility or a medical professional.

13. The system of claim 12, wherein the computer processor is further configured to optimize the treatment care path based on a quality of the one or more providers, the quality of the one or more providers based on quality assessment data.

14. The system of claim 10, the one or more treatment care paths having the same desired medical outcome.

15. The system of claim 10, the one or more treatment care paths having at least two different desired medical outcomes.

16. The system of claim 10, wherein the at least one medical service or treatment comprises at least one of an office visit, receiving a prescription for medication, a radiology appointment, or surgery.

17. The system of claim 10, wherein the cost estimate is provided by:
    determining whether the medical service or treatment is within a fee schedule of the provider, and if so, providing the cost estimate based thereon;
    where the fee schedule is unavailable, determining whether the medical service or treatment corresponds to prior claims data for the medical service or treatment administered by the provider, and if so, providing the cost estimate based thereon; or
    where the prior claims data is unavailable for the medical service or treatment offered by the provider, determining the cost estimate based on a geographic average for the medical service or treatment.

18. The system of claim 10, further comprising providing for display at least one of the optimized one or more treatment care paths, the aggregated cumulative total costs, or the estimated consumer costs for the individual steps.

19. A non-transitory computer readable medium storing instructions that when executed by a computer cause the computer to perform operations comprising:
    receiving identification of a health condition and a selection of at least one desired medical outcome after treatment of the health condition;
    identifying one or more treatment care paths, each comprising a plurality of steps over a time range to achieve the selected at least one desired medical outcome, wherein at least one step within the plurality of steps comprises at least one medical service or treatment to achieve the desired medical outcome;
    for each of the at least one medical service or treatment in the one or more treatment care paths, identifying one or more providers offering the medical service or treatment;
    for each of the one or more providers, providing a cost estimate for receiving the medical service or treatment;
    optimizing the one or more treatment care paths at least based on ranking providers offering the at least one medical service or treatment within each of the one or more treatment care paths, wherein the providers are ranked from lowest provider cost estimate to highest provider cost estimate;
    determining an estimated cumulative total cost for the optimized one or more treatment care paths, the estimated cumulative total cost comprising an estimated cost to the consumer and an estimated cost to an insurance provider;

determining at least estimated consumer costs for individual steps in the plurality of steps within each of the optimized one or more treatment care paths;

identifying where within the time range the estimated consumer costs for the individual steps will be incurred within each of the optimized one or more treatment care paths; and providing for display an indication of where the estimated consumer costs will be incurred within the time range.

20. The non-transitory computer readable medium of claim 19, the one or more treatment care paths having the same desired medical outcome.

21. The non-transitory computer readable medium of claim 19, the one or more treatment care paths having at least two different desired medical outcomes.

22. The non-transitory computer readable medium of claim 19, further comprising providing for display information related to a quality of the one or more providers, the quality of the one or more providers based on quality assessment data.

23. The non-transitory computer readable medium of claim 19, wherein the one or more providers comprise one or more of a medical facility or a medical professional.

24. The non-transitory computer readable medium of claim 19, wherein the step of optimizing is further based on a quality of the one or more providers, the quality of the one or more providers based on quality assessment data.

25. The non-transitory computer readable medium of claim 19, wherein the cost estimate is provided by:

determining whether the medical service or treatment is within a fee schedule of the provider, and if so, providing the cost estimate based thereon;

where the fee schedule is unavailable, determining whether the medical service or treatment corresponds to prior claims data for the medical service or treatment administered by the provider, and if so, providing the cost estimate based thereon; or where the prior claims data is unavailable for the medical service or treatment offered by the provider, determining the cost estimate based on a geographic average for the medical service or treatment.

26. The non-transitory computer readable medium of claim 19, further comprising providing for display at least one of the optimized one or more treatment care paths, the aggregated cumulative total costs, or the estimated consumer costs for the individual steps.

* * * * *

UNITED STATES PATENT AND TRADEMARK OFFICE
CERTIFICATE OF CORRECTION

PATENT NO. : 8,805,701 B2
APPLICATION NO. : 13/354019
DATED : August 12, 2014
INVENTOR(S) : Camacho et al.

It is certified that error appears in the above-identified patent and that said Letters Patent is hereby corrected as shown below:

In the Specification

| Column | Line | Delete | Insert |
| --- | --- | --- | --- |
| 11 | 40 | "Paths 1103e and 1103d" | --Paths 1103c and 1103d-- |

Signed and Sealed this
Twenty-third Day of December, 2014

Michelle K. Lee
*Deputy Director of the United States Patent and Trademark Office*